(12) United States Patent
Esteller et al.

(10) Patent No.: US 10,974,042 B2
(45) Date of Patent: Apr. 13, 2021

(54) SYSTEM AND METHODS FOR HEART RATE AND ELECTROCARDIOGRAM EXTRACTION FROM A SPINAL CORD STIMULATION SYSTEM

(71) Applicant: Boston Scientific Neuromodulation Corporation, Valencia, CA (US)

(72) Inventors: Rosana Esteller, Santa Clarita, CA (US); Deepa Mahajan, North Oaks, MN (US); Bhaskar Sen, St. Paul, MN (US); Tianhe Zhang, Studio City, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 45 days.

(21) Appl. No.: 16/282,130

(22) Filed: Feb. 21, 2019

(65) Prior Publication Data

US 2019/0290900 A1  Sep. 26, 2019

Related U.S. Application Data

(60) Provisional application No. 62/648,231, filed on Mar. 26, 2018.

(51) Int. Cl.
*A61B 5/00* (2006.01)
*A61B 5/0205* (2006.01)
(Continued)

(52) U.S. Cl.
CPC .......... *A61N 1/0553* (2013.01); *A61B 5/0205* (2013.01); *A61B 5/042* (2013.01);
(Continued)

(58) Field of Classification Search
CPC .............. A61N 1/0551; A61N 1/36135; A61N 1/36062; A61N 1/0205; A61B 5/725;
(Continued)

(56) References Cited

U.S. PATENT DOCUMENTS 5,697,958 A   12/1997 Paul et al.
5,702,429 A   12/1997 King
(Continued)

FOREIGN PATENT DOCUMENTS

WO   2013/154656 A1   10/2013
WO   2015/077362 A1   5/2015
(Continued)

OTHER PUBLICATIONS

International Search Report and Written Opinion regarding corresponding PCT Application No. PCT/US2019/019834, dated Nov. 13, 2019.
(Continued)

*Primary Examiner* — Carl H Layno
*Assistant Examiner* — Anh-Khoa N Dinh
(74) *Attorney, Agent, or Firm* — Lewis & Reese, PLLC

(57) ABSTRACT

A system and method for extracting a cardiac signal from a spinal signal include measuring a spinal signal at one or more electrodes that are connected to a neurostimulator and implanted within a patient's spinal canal and processing the spinal signal to extract the cardiac signal, which includes features that are representative of the patient's cardiac activity. Processing the spinal signal to extract the cardiac signal can include filtering the spinal signal using one or more filters. Model reduction schemes such as independent component analysis can additionally or alternatively be employed to extract the cardiac signal. The extracted cardiac signal can include a number of features that correspond to an electrocardiogram and can be used to determine the patient's heart rate and/or to detect a cardiac anomaly. The determined cardiac features can additionally be used to adjust parameters of the stimulation that is provided by the neurostimulator.

18 Claims, 13 Drawing Sheets

(51) Int. Cl.
*A61B 5/024* (2006.01)
*A61B 5/04* (2006.01)
*A61B 5/042* (2006.01)
*A61N 1/05* (2006.01)
*A61N 1/372* (2006.01)
*A61N 1/36* (2006.01)

(52) U.S. Cl.
CPC ........ *A61B 5/04014* (2013.01); *A61N 1/0551* (2013.01); *A61N 1/36062* (2017.08); *A61N 1/36135* (2013.01); *A61N 1/37217* (2013.01); *A61N 1/37247* (2013.01); *A61B 5/0031* (2013.01); *A61N 1/36071* (2013.01)

(58) Field of Classification Search
CPC ... A61B 5/02444; A61B 5/407; A61B 5/0031; A61B 5/6877; A61B 5/024; A61B 5/02405
USPC .......................................... 600/544, 546, 547
See application file for complete search history.

(56) References Cited

U.S. PATENT DOCUMENTS

| | | | |
|---|---|---|---|
| 5,902,236 A | 5/1999 | Iversen | |
| 5,902,249 A | 5/1999 | Lyster | |
| 5,913,882 A | 6/1999 | King | |
| 6,181,969 B1 | 1/2001 | Gord et al. | |
| 6,516,227 B1 | 2/2003 | Meadows et al. | |
| 7,024,247 B2 | 4/2006 | Gliner et al. | |
| 7,162,304 B1* | 1/2007 | Bradley | A61B 5/0402 600/509 |
| 7,366,572 B2 | 4/2008 | Heruth et al. | |
| 7,424,322 B2 | 9/2008 | Lombardi et al. | |
| 7,450,992 B1 | 11/2008 | Cameron | |
| 7,491,181 B2 | 2/2009 | Heruth et al. | |
| 7,590,455 B2 | 9/2009 | Heruth et al. | |
| 7,717,848 B2 | 5/2010 | Heruth et al. | |
| 7,853,322 B2 | 12/2010 | Bourget et al. | |
| 7,860,563 B2 | 12/2010 | Foreman et al. | |
| 7,881,798 B2 | 2/2011 | Miesel et al. | |
| 7,957,809 B2 | 6/2011 | Bourget et al. | |
| 8,255,057 B2 | 8/2012 | Fang et al. | |
| 8,335,664 B2 | 12/2012 | Eberle | |
| 8,352,030 B2 | 1/2013 | Denison | |
| 8,606,362 B2 | 12/2013 | He et al. | |
| 8,620,436 B2 | 12/2013 | Parramon et al. | |
| 8,768,453 B2 | 7/2014 | Parramon et al. | |
| 9,044,155 B2 | 6/2015 | Strahl | |
| 9,061,140 B2 | 6/2015 | Shi et al. | |
| 9,155,892 B2 | 10/2015 | Parker et al. | |
| 9,248,274 B2 | 2/2016 | Troosters et al. | |
| 9,248,279 B2 | 2/2016 | Chen et al. | |
| 9,265,431 B2 | 2/2016 | Hincapie Ordonez et al. | |
| 9,302,112 B2 | 4/2016 | Bornzin et al. | |
| 9,381,356 B2 | 7/2016 | Parker et al. | |
| 9,386,934 B2 | 7/2016 | Parker et al. | |
| 9,403,013 B2 | 8/2016 | Walker et al. | |
| 9,409,020 B2 | 8/2016 | Parker | |
| 9,526,897 B2 | 12/2016 | Chen et al. | |
| 9,533,148 B2 | 1/2017 | Carcieri et al. | |
| 9,731,116 B2 | 8/2017 | Chen | |
| 9,872,990 B2 | 1/2018 | Parker et al. | |
| 9,974,455 B2 | 5/2018 | Parker et al. | |
| 9,974,959 B2 | 5/2018 | Moffitt et al. | |
| 10,076,667 B2 | 9/2018 | Kaula et al. | |
| 2002/0156513 A1 | 10/2002 | Borkan | |
| 2005/0246004 A1 | 11/2005 | Cameron et al. | |
| 2006/0095081 A1* | 5/2006 | Zhou | A61N 1/36114 607/2 |
| 2008/0071324 A1 | 3/2008 | Miesel et al. | |
| 2008/0146894 A1 | 6/2008 | Bulkes et al. | |
| 2009/0306491 A1* | 12/2009 | Haggers | A61N 1/37229 600/373 |
| 2010/0114201 A1* | 5/2010 | Donofrio | A61B 5/7217 607/4 |
| 2010/0228310 A1 | 9/2010 | Shuros et al. | |
| 2012/0092031 A1 | 4/2012 | Shi et al. | |
| 2012/0095519 A1 | 4/2012 | Parramon et al. | |
| 2012/0095529 A1 | 4/2012 | Parramon et al. | |
| 2013/0289665 A1 | 10/2013 | Marnfeldt et al. | |
| 2014/0194772 A1 | 7/2014 | Single et al. | |
| 2014/0236042 A1 | 8/2014 | Parker et al. | |
| 2014/0296737 A1 | 10/2014 | Parker et al. | |
| 2014/0304773 A1 | 10/2014 | Woods et al. | |
| 2015/0080982 A1 | 3/2015 | Funderburk | |
| 2015/0157861 A1 | 6/2015 | Aghassian et al. | |
| 2015/0282725 A1 | 10/2015 | Single et al. | |
| 2015/0313487 A1 | 11/2015 | Single et al. | |
| 2015/0360031 A1* | 12/2015 | Bornzin | A61N 1/36071 607/62 |
| 2015/0360038 A1 | 12/2015 | Zottola et al. | |
| 2016/0166164 A1 | 6/2016 | Obradovic et al. | |
| 2016/0287126 A1 | 10/2016 | Parker et al. | |
| 2016/0287182 A1 | 10/2016 | Single et al. | |
| 2017/0049345 A1 | 2/2017 | Single et al. | |
| 2017/0071490 A1 | 3/2017 | Parker et al. | |
| 2017/0135624 A1 | 5/2017 | Parker et al. | |
| 2017/0216587 A1 | 8/2017 | Parker et al. | |
| 2017/0296810 A1 | 10/2017 | Thakur et al. | |
| 2017/0296823 A1 | 10/2017 | Hershey et al. | |
| 2017/0361101 A1 | 12/2017 | Single et al. | |
| 2018/0071527 A1 | 3/2018 | Feldman et al. | |
| 2018/0110987 A1 | 4/2018 | Parker et al. | |
| 2018/0117335 A1 | 5/2018 | Parker et al. | |
| 2018/0132747 A1 | 5/2018 | Parker et al. | |
| 2018/0132760 A1 | 5/2018 | Parker et al. | |
| 2018/0133459 A1 | 5/2018 | Parker et al. | |
| 2018/0140831 A1 | 5/2018 | Feldman et al. | |
| 2018/0192942 A1 | 7/2018 | Clark et al. | |
| 2018/0228391 A1 | 8/2018 | Parker et al. | |
| 2018/0228547 A1 | 8/2018 | Parker et al. | |
| 2018/0256052 A1 | 9/2018 | Parker et al. | |
| 2019/0099602 A1 | 4/2019 | Esteller et al. | |

FOREIGN PATENT DOCUMENTS

| | | |
|---|---|---|
| WO | 2017/044904 A1 | 3/2017 |
| WO | 2017/100866 | 6/2017 |
| WO | 2017/173493 | 10/2017 |
| WO | 2017/184993 A1 | 10/2017 |
| WO | 2017/210352 A1 | 12/2017 |
| WO | 2017/219096 | 12/2017 |

OTHER PUBLICATIONS

"Marker for Pain Using Vital Signs for SCS Systems," Research Disclosure, No. 637028, Digitally Published on Apr. 5, 2017, 2 pages.
U.S. Appl. No. 62/568,211, filed Oct. 4, 2017.
Invitation to Pay Additional Fees regarding corresponding PCT Application No. PCT/US2019/019834, dated Apr. 18, 2019.
U.S. Appl. No. 62/641,748, filed Mar. 12, 2018, Zhu et al.
U.S. Appl. No. 62/648,231, filed Mar. 26, 2018, Esteller et al.
U.S. Appl. No. 62/650,844, filed Mar. 30, 2018, Marnfeldt et al.
U.S. Appl. No. 62/679,259, filed Jun. 1, 2018, Esteller et al.
U.S. Appl. No. 62/768,617, filed Nov. 16, 2018, Esteller et al.
U.S. Appl. No. 62/825,982, filed Mar. 29, 2019, Wagenbach et al.
U.S. Appl. No. 16/210,794, filed Dec. 5, 2018, Brill et al.
U.S. Appl. No. 16/238,151, filed Jan. 2, 2019, Esteller et al.
H. Mino & J. Rubenstein, "Effects of Neural Refractoriness on Spatio-Temporal Variability in Spike Initiations with Eletrical Stimulation," IEEE Trans. on Neural Sys. & Rehabilitation Eng., vol. 14, No. 3, pp. 273-280 (2006).
M. Moffit et al., A Novel 3-Dimensional Algorithm for Model-Based Programming in Spinal presentation Cord Stimulation (SCS): Illumina-3D™, presentation (2013).
M. Hughes, "Fundamentals of Clinical ECAP Measures in Cochlear Implants: Part 1: Use of the ECAP in Speech Processor Programming (2nd Ed.)," Audiology Online (Nov. 8, 2010). (http:// www.

(56) References Cited

OTHER PUBLICATIONS audiologyonline.com/ articles/ fundamentalsclinicalecapmeasurein846).
I. Akhoun et al., "Electrically evoked compound action potential artifact rejection by independent component analysis: Technique validation," Hearing Research 302, pp. 60-73 (2013).
J. Rubinstein et al., "Pseudospontaneous activity: stochastic independence of auditory nerve fibers with electrical stimulation," Hear Res., 127(1-2), pp. 108-118 (1999) (abstract only).
J. Paz, "Physiological Midline Mapping Based on Spinal Cord Stimulation (SCS) Response Using the 32-Contact Paddle Lead," 19$^{th}$ NANS Annual Meeting (Dec. 13-15, 2015).
E.L. Air et al., "Electrophysiologic Monitoring for Placement of Laminectomy Leads for Spinal Cord Stimulation Under General Anesthesia," Neuromodulation: Technology at the Neural Interface, vol. 15(6), pp. 573-580 (2012).
J.L. Shils et al., "Intraoperative Neurophysiologic Methods for Spinal Cord Stimulator Placement Under General Anesthesia," Neuromodulation: Technology at the Neural Interface, vol. 15(6), pp. 560-572 (2012).
A. Taghva et al., "Intraoperative Electromyography as an Adjunct to Sacral Neuromodulation for Chronic Pelvic Pain," Neuromodulation: Technology at the Neural Interface, vol. 18(1), pp. 62-66 (2015).

\* cited by examiner

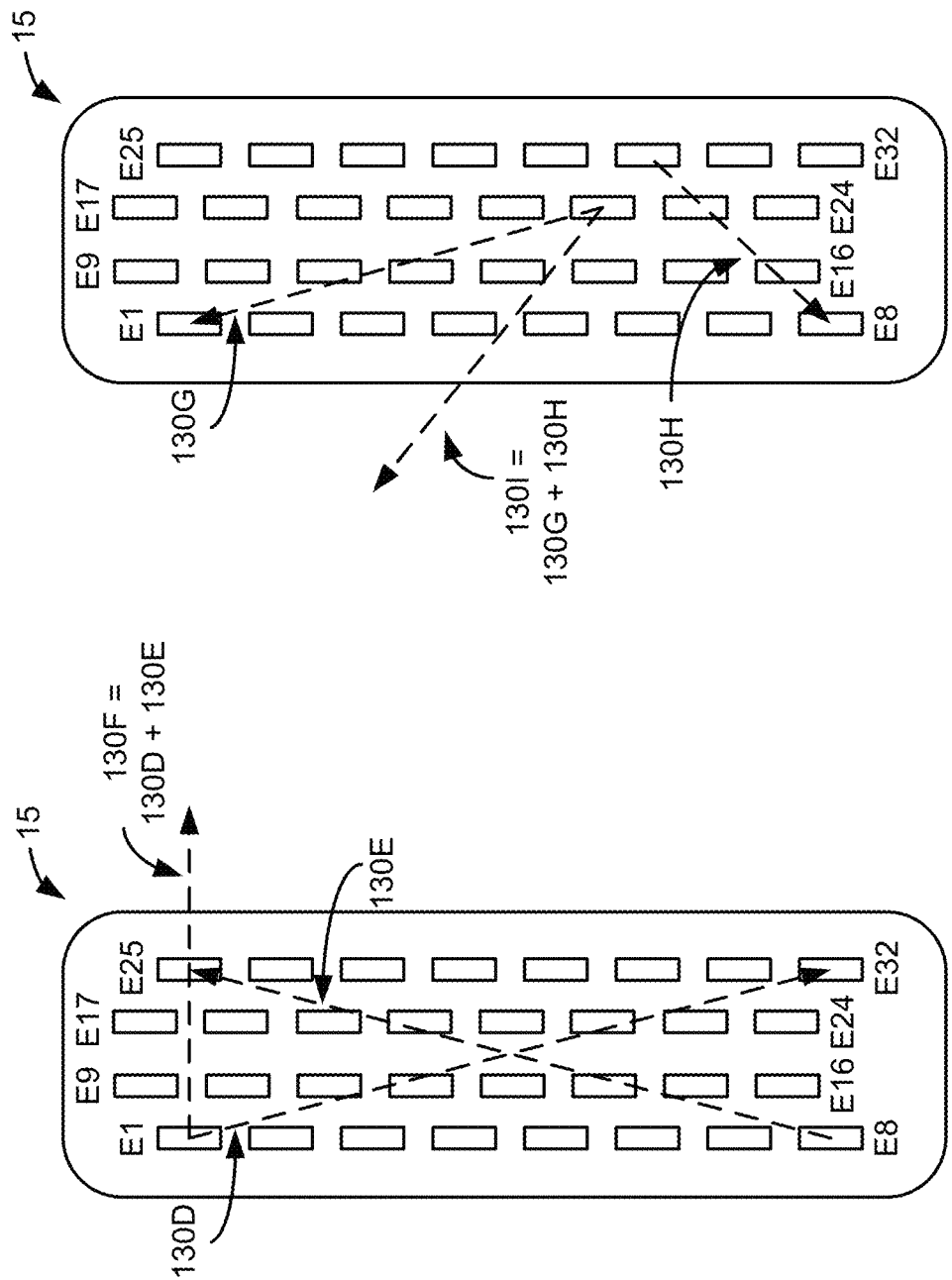

SYSTEM AND METHODS FOR HEART RATE AND ELECTROCARDIOGRAM EXTRACTION FROM A SPINAL CORD STIMULATION SYSTEM

CROSS REFERENCE TO RELATED APPLICATIONS

This is a non-provisional application of U.S. Provisional Patent Application Ser. No. 62/648,231, filed Mar. 26, 2018, to which priority is claimed, and which is incorporated herein by reference in its entirety.

FIELD OF THE TECHNOLOGY

Implantable stimulation devices deliver electrical stimuli to nerves and tissues for the therapy of various biological disorders. The present application is related to a technique to extract data relating to a patient's cardiac activity from a Spinal Cord Stimulation (SCS) system.

INTRODUCTION

An SCS system typically includes an implantable medical device (IMD), or, more specifically, an implantable pulse generator (IPG) 10 shown in plan and cross-sectional views in FIGS. 1A and 1B. The IPG 10 includes a biocompatible device case 30 that is configured for implantation in a patient's tissue that holds the circuitry and battery 36 (FIG. 1B) necessary for the IPG to function. The IPG 10 is coupled to electrodes 16 via one or more electrode leads 14 that form an electrode array 12. The electrodes 16 are configured to contact a patient's tissue and are carried on a flexible body 18, which also houses the individual lead wires 20 coupled to each electrode 16. The lead wires 20 are also coupled to proximal contacts 22, which are insertable into lead connectors 24 fixed in a header 28 on the IPG 10, which header can comprise an epoxy for example. Once inserted, the proximal contacts 22 connect to header contacts 26 in the lead connectors 24, which are in turn coupled by electrode feedthrough pins 34 through an electrode feedthrough 32 to circuitry within the case 30 (connection not shown).

In the illustrated IPG 10, there are thirty-two lead electrodes (E1-E32) split between four leads 14, with the header 28 containing a 2×2 array of lead connectors 24 to receive the leads' proximal ends. However, the number of leads and electrodes in an IPG is application specific and therefore can vary. In a SCS application, the electrode leads 14 are typically implanted proximate to the dura in a patient's spinal cord, and when a four-lead IPG 10 is used, these leads can be split with two on each of the right and left sides. Two 16-electrode leads could also be used with each having a splitter allowing the leads to be connected to two lead connectors 24. Each of the IPG's lead connectors 24 could also support different numbers of electrodes, such as 12 or 16 electrodes. The proximal contacts 22 are tunneled through the patient's tissue to a distant location such as the buttocks where the IPG case 30 is implanted, at which point they are coupled to the lead connectors 24. As also shown in FIG. 1A, one or more flat paddle leads 15 can also be used with IPG 10, and in the example shown thirty two electrodes 16 are positioned on one of the generally flat surfaces of the head 17 of the paddle lead, which surface would face the dura when implanted. In other IPG examples designed for implantation directly at a site requiring stimulation, the IPG can be lead-less, having electrodes 16 instead carried by the case of the IPG for contacting the patient's tissue.

As shown in the cross section of FIG. 1B, the IPG 10 includes a printed circuit board (PCB) 40. Electrically coupled to the PCB 40 are the battery 36, which in this example is rechargeable; other circuitry 46 coupled to top and/or bottom surfaces of the PCB 40, including a microcontroller or other control circuitry necessary for IPG operation; and a charging coil 44 for wirelessly receiving a magnetic charging field from an external charger (not shown) for recharging the battery 36. If battery 36 is permanent and not rechargeable, charging coil 44 would be unnecessary.

The IPG 10 also includes one or more antennas 42a and 42b for transcutaneously communicating with external programming devices, such as a patient external controller 50 (FIG. 2) or a clinician programmer 90 (FIG. 3), which is provided via the execution of software on a clinician programmer computer 96. While illustrated as a dedicated device, the patient external controller 50 can take the form of an application that resides on a smart device, such as smart phone or other portable device. Antennas 42a and 42b are different in shape and in the electromagnetic fields they employ. Telemetry antenna 42a comprises a coil, which can bi-directionally communicate with an external device via a magnetic induction communication link. Telemetry antenna 42b comprises a short-range Radio-Frequency (RF) antenna that operates in accordance with a short-range RF communication standard, such as Bluetooth, BLE, NFC, Zigbee, WiFi (802.11x), and the Medical Implant Communication Service (MICS) or the Medical Device Radiocommunications Service (MDRS). As will be understood, external devices such as external controller 50 and clinician programmer 90 include similar communication circuitry (e.g., antenna(s), modulation and demodulation circuitry, etc.) such that a communication link can be established between the external device and the IPG 10.

Implantation of IPG 10 in a patient is normally a multi-step process, as explained with reference to FIG. 3. A first step involves implantation of the distal ends of the lead(s) 14 or 15 with the electrodes 16 into the epidural space of the spinal canal 60 of the patient through a temporary incision 62 in the patient's tissue 5. (Only two leads 14 with sixteen total electrodes 16 are shown in FIG. 3 for simplicity). The proximal ends of the leads 14 or 15 including the proximal contacts 22 extend externally from the incision 62 (i.e., outside the patient), and are ultimately connected to an External Trial Stimulator (ETS) 70. The ETS 70 is used during a trial stimulation phase to provide stimulation to the patient, which may last for two or so weeks for example. To facilitate the connection between the leads 14 or 15 and the ETS 70, ETS extender cables 80 may be used that include receptacles 82 (similar to the lead connectors 24 in the IPG 10) for receiving the proximal contacts 22 of leads 14 or 15, and connectors 84 for meeting with ports 72 on the ETS 70, thus allowing the ETS 70 to communicate with each electrode 16 individually. Once connected to the leads 14 or 15, the ETS 70 can then be affixed to the patient in a convenient fashion for the duration of the trial stimulation phase, such as by placing the ETS 70 into a belt worn by the patient (not shown). ETS 70 includes a housing 73 for its control circuitry, antenna, etc., which housing 73 is not configured for implantation in a patient's tissue.

The ETS 70 essentially mimics operation of the IPG 10 to provide stimulation to the implanted electrodes 16, and thus includes contains a battery within its housing along with stimulation and communication circuitry similar to that provided in the IPG 10. Thus, the ETS 70 allows the effectiveness of stimulation therapy to be verified for the patient, such as whether therapy has alleviated the patient's symptoms (e.g., pain). Trial stimulation using the ETS 70 further allows for the determination of particular stimulation programs that seem promising for the patient to use once the IPG 10 is later implanted into the patient. A stimulation program may include stimulation parameters that specify for example: which of the electrodes 16 are to be active and used to issue stimulation pulses; the polarity of those active electrodes (whether they are to act as anodes or cathodes); the current or voltage amplitude (A) of the stimulation pulses; the pulse width (PW) of the stimulation pulses; the frequency (f) of the stimulation pulses; the duty cycle (DC) of the stimulation pulses (i.e., the percentage of time that the pulses are asserted relative to the period of the pulses) the shape of the stimulation waveform (e.g., one or more square pulses, one or more ramped pulses, one or more sinusoidal pulses, or even non-pulse-based waveforms, etc.); and other parameters related to issuing a burst of pulses, such as the number of pulses; etc.

At the end of the trial stimulation phase, a decision is made whether to abandon stimulation therapy, or whether to provide the patient with a permanent IPG 10 such as that shown in FIGS. 1A and 1B. Should it be determined that stimulation therapy is not working for the patient, the leads 14 or 15 can be explanted from the patient's spinal column 60 and incision 62 closed in a further surgical procedure. By contrast, if stimulation therapy is effective, IPG 10 can be permanently implanted in the patient as discussed above. ("Permanent" in this context generally refers to the useful life of the IPG 10, which may be from a few years to a few decades, at which time the IPG 10 would need to be explanted and a new IPG 10 implanted). Thus, the IPG 10 would be implanted in the correct location (e.g., the buttocks) and connected to the leads 14 or 15, and then temporary incision 62 can be closed and the ETS 70 dispensed with. The result is a fully-implanted stimulation therapy solution. If a particular stimulation program(s) had been determined as effective during the trial stimulation phase, it/they can then be programmed into the IPG 10, and thereafter modified wirelessly, using either the external controller 50 or the clinician programmer 90.

An example of stimulation pulses as prescribed by a particular stimulation program and as executable by the IPG or ETS 70 is illustrated in FIG. 4. In the example shown, each stimulation pulse is biphasic, meaning it comprises a first pulse phase followed essentially immediately thereafter by an opposite polarity pulse phase. The pulse width (PW) could comprise the duration of either of the pulse phases individually as shown, or could comprise the entire duration of the biphasic pulse including both pulse phases. The frequency (f) and amplitude (A) of the pulses is also shown. Although not shown, monophasic pulses—having only a first pulse phase but not followed by an active-charge recovery second pulse phase—can also be used.

Biphasic pulses are useful because the second pulse phase can actively recover any charge build up after the first pulse phase residing on capacitances (such as the DC-blocking capacitors 107 discussed later) in the current paths between the active electrodes. In the example stimulation program shown in FIG. 4, electrode E4 is selected as the anode electrode while electrode E5 is selected as the cathode electrode (during the first pulse phase), which because two electrodes 16 are implicated, comprises what is known as bipolar stimulation. The pulses as shown comprise pulses of constant current, and notice that the amplitude of the current at any point in time is equal but opposite such that current injected into the patient's tissue by one electrode (e.g., E4) is removed from the tissue by the other electrode (E5). Notice also that the area of the first and second pulse phases are equal, ensuring active charge recovery of the same amount of charge during each pulse phase. Although not shown, more than two electrodes can be active at any given time. For example, electrode E4 could comprise an anode providing a +10 mA current pulse amplitude, while electrodes E3 and E5 could both comprise cathodes with −7 mA and −3 mA current pulse amplitudes respectively. Biphasic pulses are particularly beneficial when pulses are issued at higher frequencies, although they may be used at lower frequencies as well.

The stimulation program executed by the IPG 10 and ETS 70 can be set or adjusted via a communication link from the external controller 50 (FIG. 2) or clinician programmer 90 (FIG. 3). While the external controller 50's antenna is usually within its housing, the clinician programmer 90 may include a communication head or wand 94 containing an antenna and wired to computer 92. Further details concerning the clinician programmer 90 may be as described in U.S. Patent Application Publication 2015/0360038, and further details concerning an external controller can be found in U.S. Patent Application Publication 2015/0080982. As is known, both of the external communication devices have graphical user interfaces that can be used by the clinician or patient to set and adjust the stimulation program that the IPG 10 or ETS 70 will run.

SUMMARY

A system is disclosed comprising measurement circuitry configured to measure a spinal signal at one or more electrodes that are connectable to a neurostimulator and implantable within a patient's spinal canal; and processing circuitry configured to process the spinal signal to extract a cardiac signal that comprises one or more features that are representative of the patient's cardiac activity. At least one of the measurement circuitry or the processing circuitry may be within the neurostimulator. The system may further include control circuitry configured to control stimulation circuitry to provide electrical stimulation to neural tissue, and the control circuitry may be further configured to adjust parameters of the electrical stimulation based on one or more properties of the cardiac signal.

The processing circuitry may be further configured to process the spinal signal by performing a first filtering operation using a low-pass filter; and performing a second filtering operation using a moving average filter. The processing circuitry may be further configured to process the spinal signal by extracting a subcomponent of the spinal signal using a model reduction scheme. The model reduction scheme may include independent component analysis.

The spinal signal may include a monopolar spinal signal that is measured as a differential voltage between one of the electrodes and a reference voltage. The spinal signal may include a bipolar spinal signal that is measured as a differential voltage between two of the electrodes. The spinal signal may include an arithmetic combination of two or more bipolar spinal signals that are each measured as a differential voltage between two of the electrodes, and the two or more bipolar spinal signals may be selected to obtain a desired directionality of the spinal signal.

The processing circuitry may be configured to determine the patient's heart rate based on the cardiac signal. The processing circuitry may be further configured to detect a cardiac anomaly based on the cardiac signal, and the system may further include control circuitry configured to communicate an indication of the cardiac anomaly to the patient.

A system is disclosed comprising a non-transitory computer-readable medium comprising instructions to cause first control circuitry in a computing device to present a graphical user interface that is configured to receive one or more first user settings associated with extracting, from a spinal signal, a cardiac signal that comprises one or more features that are representative of a patient's cardiac activity; second control circuitry in an implantable medical device, the second control circuitry configured to measure a spinal signal at one or more electrodes connectable to the implantable medical device and implantable within a patient's spinal canal; and third control circuitry configured to process the spinal signal to extract the cardiac signal.

The second control circuitry in the implantable medical device may be further configured to control stimulation circuitry to provide electrical stimulation to neural tissue. The graphical user interface may be further configured to receive one or more second user settings associated with adjusting parameters of the electrical stimulation based on the extracted cardiac signal. Processing the spinal signal to extract the cardiac signal may be based on the one or more first user settings, wherein the one or more first user settings may include a selection of one of a plurality of cardiac signal extraction techniques. The one or more of the plurality of cardiac signal extraction techniques may cause the second control circuitry in the implantable medical device to process the spinal signal by performing a first filtering operation using a low-pass filter; and performing a second filtering operation using a moving average filter. The one or more of the plurality of cardiac signal extraction techniques may cause the second control circuitry in the implantable medical device to process the spinal signal by extracting a subcomponent of the spinal signal using a model reduction scheme. The model reduction scheme may include independent component analysis.

Measuring the spinal signal at one or more electrodes may be based on the one or more first user settings, wherein the one or more first user settings comprise one or more electrode settings that specify the one or more electrodes that are used to measure the spinal signal. The one or more electrode settings may specify a monopolar spinal signal that is measured as a differential voltage between one of the electrodes and a reference voltage. The one or more electrode settings may specify a bipolar spinal signal that is measured as a differential voltage between two of the electrodes. The one or more electrode settings may specify an arithmetic combination spinal signal that is composed of two or more bipolar spinal signals that are each measured as a differential voltage between two of the electrodes, and the two or more bipolar spinal signals may be selected to obtain a desired directionality of the spinal signal.

The third control circuitry may be further configured to determine the patient's heart rate based on the cardiac signal. The third control circuitry may be further configured to detect a cardiac anomaly based on the cardiac signal. The third control circuitry may be further configured to communicate an indication of the cardiac anomaly to the patient. The third control circuitry may be in the implantable medical device.

A method is disclosed comprising measuring a spinal signal at one or more electrodes that are connectable to a neurostimulator and implantable within a patient's spinal canal; and processing the spinal signal to extract a cardiac signal that comprises one or more features that are representative of the patient's cardiac activity.

A system is disclosed comprising measurement circuitry configured to measure a spinal signal at one or more electrodes that are connectable to a neurostimulator and implantable within a patient's spinal canal; and processing circuitry configured to process the spinal signal using one or more of a low-pass filter, a moving average filter, or a model reduction scheme to extract a cardiac signal that comprises one or more features that are representative of the patient's cardiac activity. At least one of the measurement circuitry or the processing circuitry may be within the neurostimulator. The system may further include control circuitry configured to control stimulation circuitry to provide electrical stimulation to neural tissue, and the control circuitry may be further configured to adjust parameters of the electrical stimulation based on one or more properties of the cardiac signal.

The processing circuitry may be further configured to process the spinal signal by performing a first filtering operation using the low-pass filter; and performing a second filtering operation using the moving average filter. The processing circuitry may be further configured to process the spinal signal by extracting a subcomponent of the spinal signal using the model reduction scheme. The model reduction scheme may include independent component analysis.

The spinal signal may include a monopolar spinal signal that is measured as a differential voltage between one of the electrodes and a reference voltage. The spinal signal may include a bipolar spinal signal that is measured as a differential voltage between two of the electrodes. The spinal signal may include an arithmetic combination of two or more bipolar spinal signals that are each measured as a differential voltage between two of the electrodes, and the two or more bipolar spinal signals may be selected to obtain a desired directionality of the spinal signal.

The processing circuitry may be configured to determine the patient's heart rate based on the cardiac signal. The processing circuitry may be further configured to detect a cardiac anomaly based on the cardiac signal, and the system may further include control circuitry configured to communicate an indication of the cardiac anomaly to the patient.

A method is disclosed comprising measuring a spinal signal at one or more electrodes that are connectable to a neurostimulator and implantable within a patient's spinal canal; and processing the spinal signal using one or more of a low-pass filter, a moving average filter, or a model reduction scheme to extract a cardiac signal that comprises one or more features that are representative of the patient's cardiac activity.

BRIEF DESCRIPTION OF THE DRAWINGS

FIG. 6 additionally shows various constituents of the spinal signal.

FIGS. 12 through 14 show example bipolar spinal vectors and the combination of the bipolar spinal vectors in accordance with an example of the disclosure.

DETAILED DESCRIPTION

While the primary function of the SCS electrodes 16 is to deliver electrical stimulation, the electrodes 16 can also be used to sense electrical activity in the area around the spinal cord. The inventors have determined that this electrical activity includes information about the patient's cardiac activity, which can be extracted from the sensed electrical activity as described below.

Figure 1A:
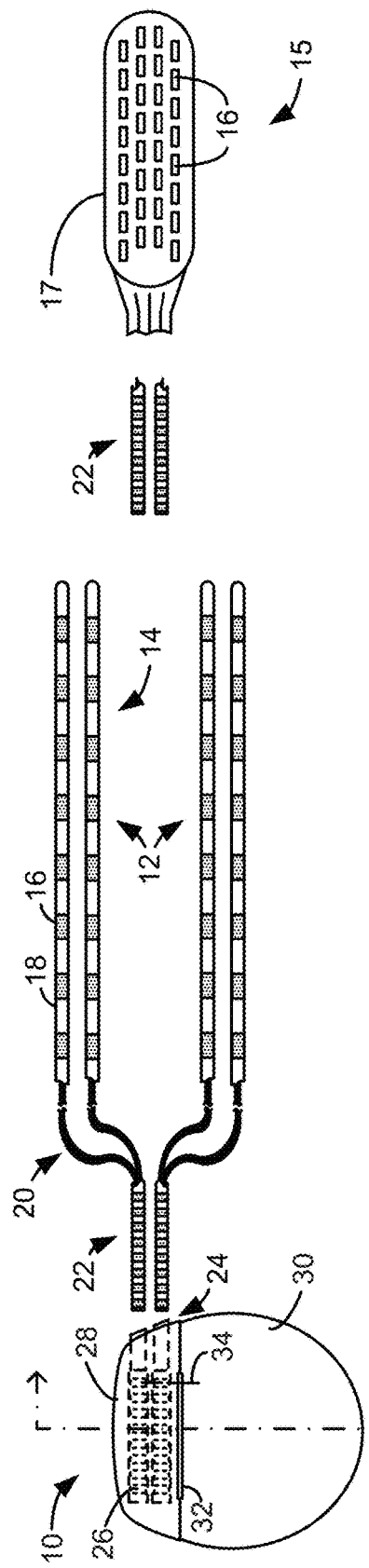
FIGS. 1A and 1B respectively show an Implantable Pulse Generator (IPG) in plan and cross sectional views.
Figure 1B:
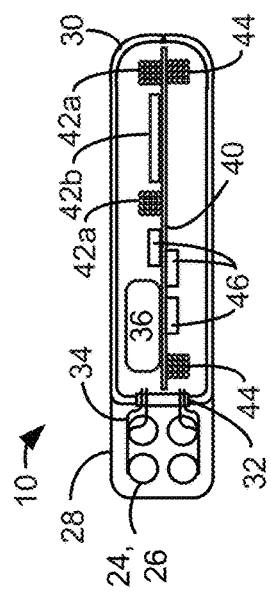
Figure 2:
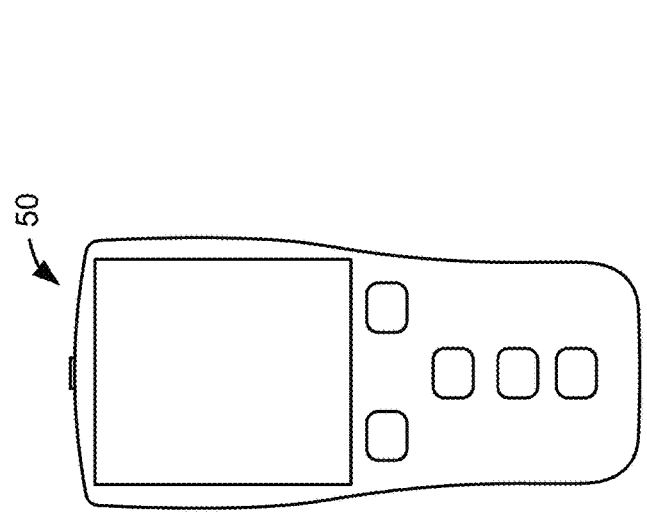
FIG. 2 shows a hand-held external controller for communicating with an IPG.
Figure 3:
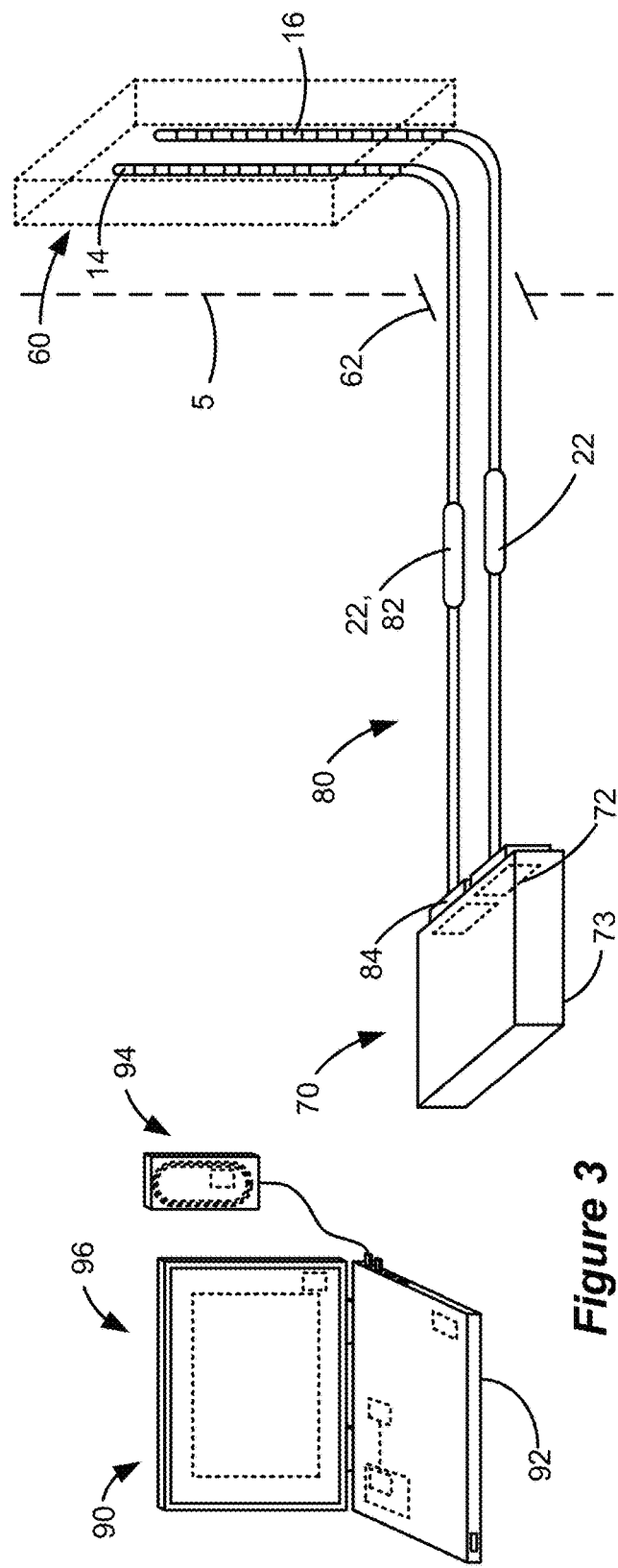
FIG. 3 shows a clinician programming system for communicating with an IPG or an External Trial Stimulator (ETS).
Figure 4:
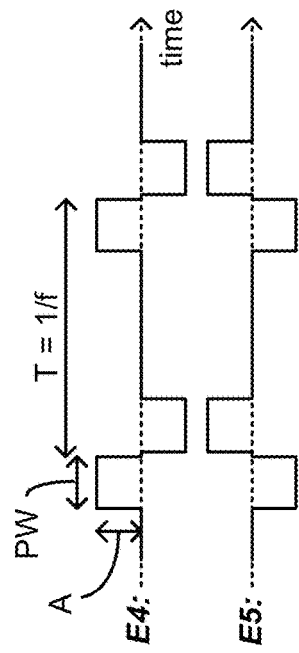
FIG. 4 shows example pulses in a stimulation program.
Figure 5:
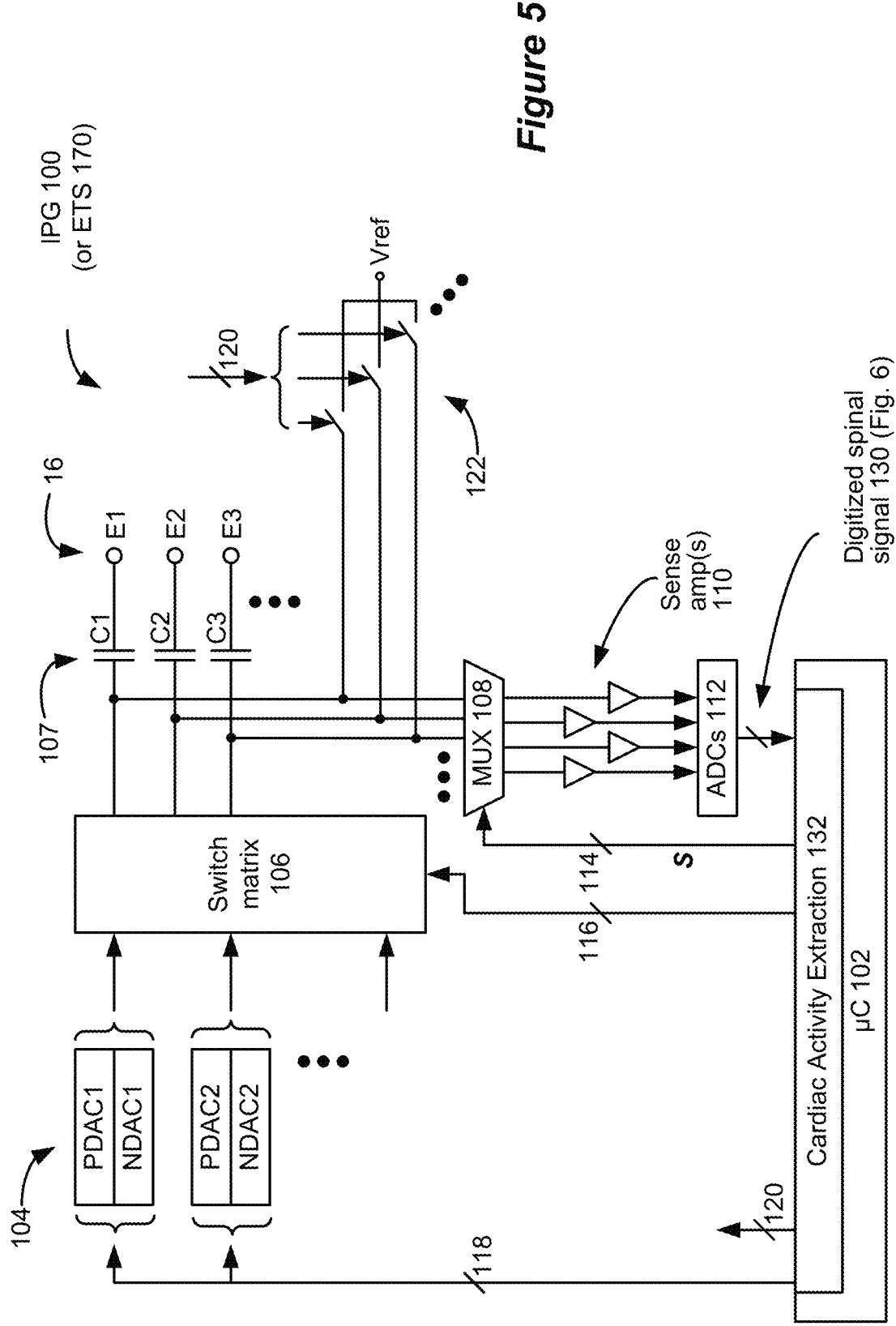
FIG. 5 shows an improved IPG (or ETS) that includes control circuitry programmed with a cardiac activity extraction algorithm, and further including sensing circuitry for sensing electrical signals at the implanted electrodes in accordance with an example of the disclosure.

FIG. 5 is a block diagram that illustrates an example of the components in an improved IPG 100 that includes sensing capability. In many aspects, the IPG 100 mirrors the IPG 10 (e.g., includes communication circuitry to communicate with external devices such as external controller 50 and/or clinician programmer 90, connects to electrode leads in the same manner, etc.), but unlike IPG 10, IPG 100 includes additional circuitry to enable sensing at its connected electrodes 16. Although described in the context of an IPG 100, it should be realized that the disclosed technique could also be operable in any neurostimulator, such as an External Trial Stimulator 170 that generally mimics the operation of IPG 100.

The IPG 100 (or ETS 170) includes control circuitry 102 into which a cardiac activity extraction algorithm can be programmed. Control circuitry 102 may comprise a microcontroller such as Part Number MSP430, manufactured by Texas Instruments. Other types of control circuitry may be used in lieu of a microcontroller as well, such as microprocessors, FPGAs, DSPs, or combinations of these, etc. Control circuitry 102 may also be formed in whole or in part in one or more Application Specific Integrated Circuits (ASICs), as described in U.S. Patent Application Publication 2012/0095529 and U.S. Pat. Nos. 9,061,140 and 8,768,453.

In the IPG 100 (or ETS 170) a bus 118 provides digital control signals to one or more Digital-to-Analog converters (DACs) 104, which are used to produce currents or voltages of prescribed amplitudes (A) for the stimulation pulses, and with the correct timing (PW, f). As shown, the DACs include both PDACs, which source current to one or more selected anode electrodes, and NDACs, which sink current from one or more selected cathode electrodes. In this example, a switch matrix 106 under control of bus 116 is used to route the output of one or more PDACs and one or more NDACs to any of the electrodes, which effectively selects the anode and cathode electrodes. The control circuitry 102 thus controls stimulation circuitry (e.g., DACs 104 and switch matrix 106) via control signals provided over the buses 118 and 116 to provide stimulation to a patient's neural tissue. The illustrated circuitry for producing stimulation pulses and delivering them to the electrodes is merely one example. Other approaches may be found for example in U.S. Pat. Nos. 8,606,362 and 8,620,436. Note that a switch matrix 106 isn't required, and instead a PDAC and NDAC can be dedicated to (e.g., wired to) each electrode.

Notice that the current paths to the electrodes 16 include the DC-blocking capacitors 107 alluded to earlier, which provide additional safety by preventing the inadvertent supply of DC current to an electrode and to a patient's tissue. As discussed earlier, capacitances such as these can become charged as stimulation currents are provided, providing an impetus for the use of biphasic pulses.

As described above, in addition to providing stimulation, the electrodes 16 can be used to sense the electrical activity in the area of the spinal cord, and thus each electrode is further coupleable to at least one sense amp 110. In the example shown, there are four sense amps 110 each corresponding to a particular timing channel in which stimulation can be issued. Under control by bus 114, a multiplexer 108 can couple any of the electrodes to any of the sense amps 110 at a given time. This is however not strictly necessary, and instead each electrode can be coupleable to its own dedicated sense amp 110, or all electrodes can be selected for sensing at different times and presented by MUX 108 to a single sense amp 110. The measured analog waveform, which may represent a differential voltage between two electrodes 16 (a bipolar spinal signal) or between a single electrode 16 and a reference voltage such as the IPG 100's case (a monopolar spinal signal), is preferably converted to a digital spinal signal 130 by one or more Analog-to-Digital converters (ADC(s)) 112, which may sample the waveform at 50 kHz for example. The ADC(s) may also reside within the control circuitry 102, particularly if the control circuitry 102 has A/D inputs.

Notice that connection of the electrodes 16 to the sense amp(s) 110 preferably occurs through the DC-blocking capacitors 107, such that capacitors are between the electrodes 16 and the sense amp(s) 110. This is preferred so as to not undermine the safety provided by the DC-blocking capacitors 107. The digitized spinal signal 130 is provided to the control circuitry 102, which processes the spinal signal 130 in accordance with a cardiac activity extraction algorithm 132. The control circuitry 102 is thus configured to measure a spinal signal at one or more electrodes that are connected to the IPG 100. As used herein, a spinal signal refers to a signal that is measured via one or more electrodes that are implanted within the epidural space of a patient's spinal column. While cardiac activity extraction is described and illustrated as being performed in the digital domain, processing of the spinal signals 130 could also be performed via analog devices directly on the measured analog signals (i.e., before the signals are processed by the ADCs 112). The circuitry illustrated in FIG. 5 includes measurement circuitry for measuring a spinal signal 130, processing circuitry for extracting a cardiac signal from the spinal signal 130, stimulation circuitry for delivering electrical stimulation to the patient's neural tissue via the electrodes 16, and control circuitry for controlling these different functional circuits. The circuitry for performing these various functions may be described based on the circuitry's specific functionality (e.g., measurement circuitry, processing circuitry, etc.) or more generally as control circuitry.

Figure 6:
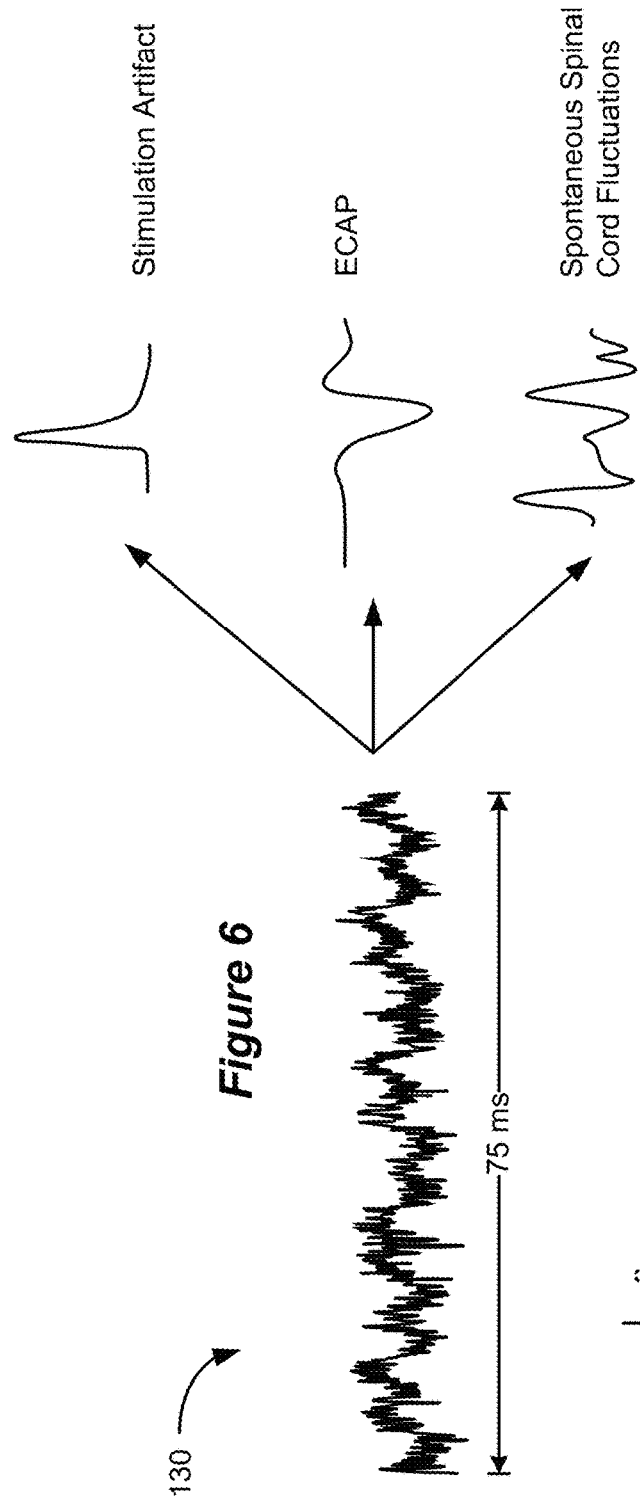
FIG. 6 shows an example spinal signal that might be measured at one or more electrodes that are implanted within a patient's spinal column in accordance with an example of the disclosure.

FIG. 6 shows an example of a spinal signal 130 over a 75 ms duration. The components that make up the spinal signal 130 include stimulation artifacts, evoked compound action potentials (ECAPs), spontaneous spinal cord fluctuations, cardiac signals, and possibly other types of signals. Stimulation artifacts are observed as a result of the electric field created in the tissue when stimulation is provided via electrodes 16. An ECAP is the cumulative response of neural fibers that are recruited as a result of the electric field generated through stimulation. Spontaneous spinal cord fluctuations are not fully understood, but they are believed to be the result of numerous different nervous systems communications. The inventors have determined that the cardiac signals contain information regarding the patient's cardiac activity and can be extracted from the spinal signal 130.

Figure 7:
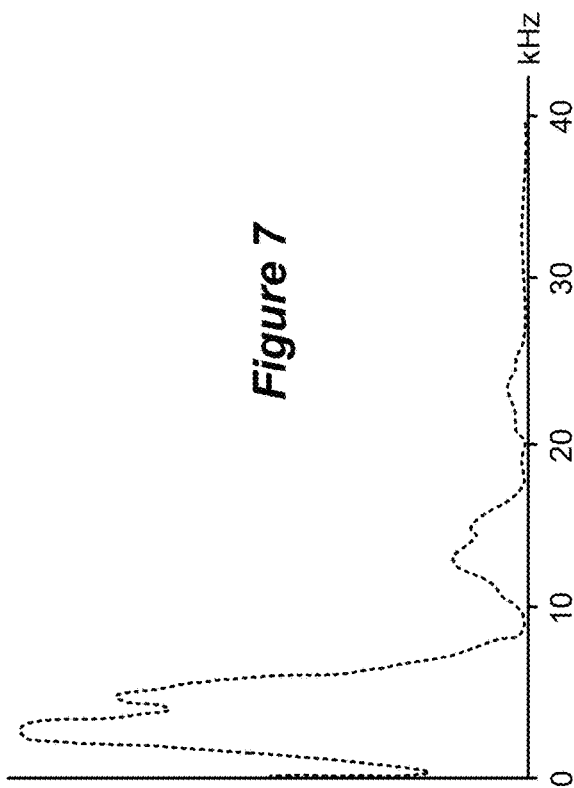
FIG. 7 shows the frequency distribution of an example spinal signal in accordance with an example of the disclosure.
Figure 8:
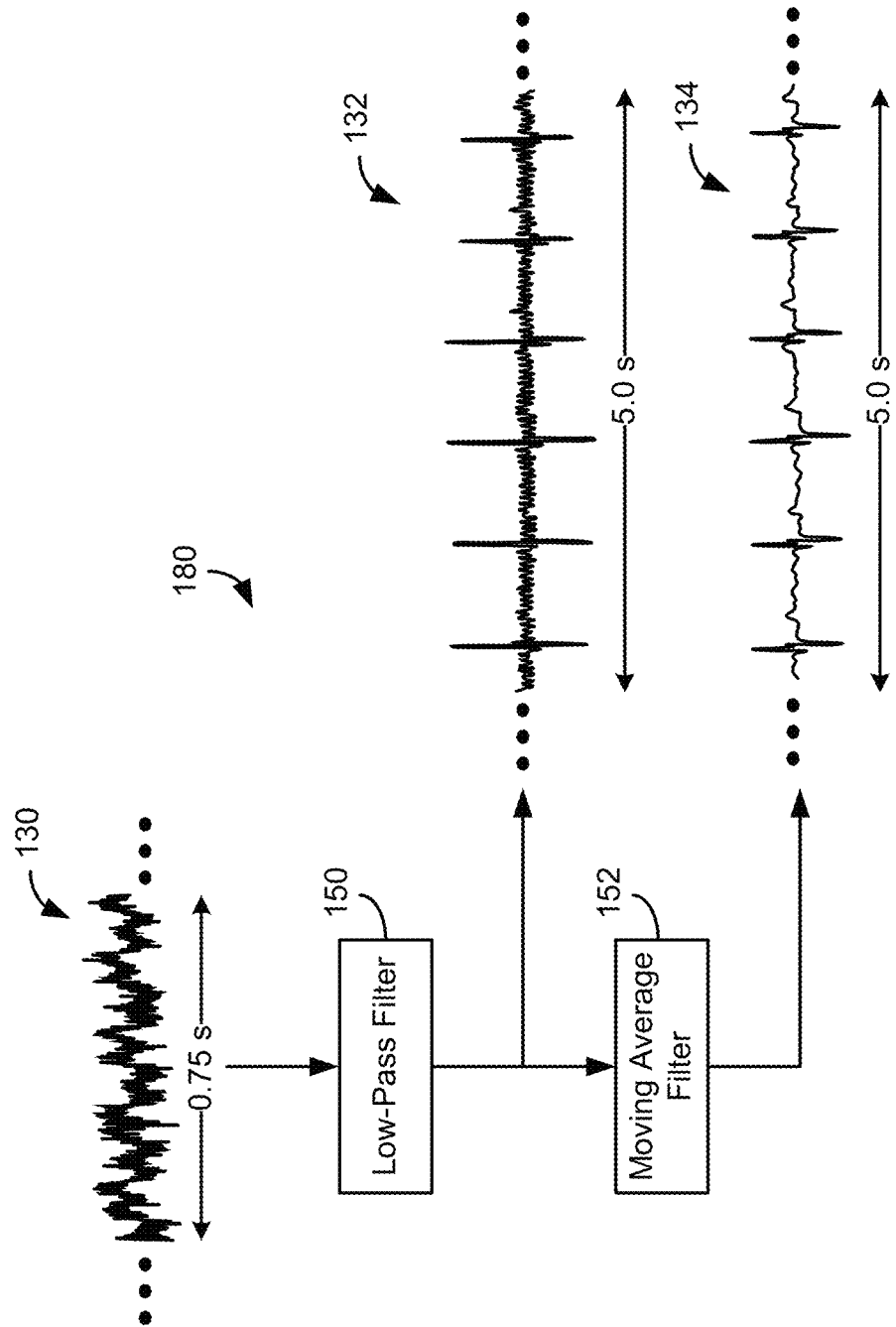
FIG. 8 shows a process for extracting a cardiac signal from a spinal signal that is measured at one or more electrodes that are implanted within a patient's spinal column in accordance with an example of the disclosure.

FIG. 7 shows the frequency distribution of an example spinal signal 130. The spinal signal 130 is primarily comprised of higher frequency components than the frequency components of the cardiac signal, which are primarily between 0 and 50 Hz, and in the case of high frequency ECG potentials may be up to 500 Hz. Thus, an initial step in a process 180 (FIG. 8) to extract the cardiac signal from the spinal signal 130, which process 180 may form part of the cardiac activity extraction algorithm 132, is to process the spinal signal 130 using a low pass filter 150. In one embodiment, the low pass filter has a pass band cutoff of 80 Hz and a stop band cutoff of 100 Hz, but it will be understood that these filter settings can be adjusted to obtain different results. The resulting filtered spinal signal 132 includes peaks that correspond to the patient's heart rate. While the peaks in the filtered signal 132 provide information regarding the patient's heart rate, the portions of the signal between the peaks are relatively noisy as a result of low frequency components in the signal 130 that may be related to cardiac activity, wander baseline movement, or power line noise. To reduce random components typical from movement wander noise, the filtered signal 132 is processed using a moving average filter 152. In one embodiment, the moving average filter 152 averages 30 sample points from the signal 132 to derive each point in the cardiac signal 134 for a 50 kHz sampling rate of the original spinal signal 130, but other numbers of sample points could also be used. As shown in FIG. 8, the random noise between the peaks in the filtered signal 132 is absent in the cardiac signal 134, which exposes additional information regarding the patient's cardiac activity as described below.

Figure 9:
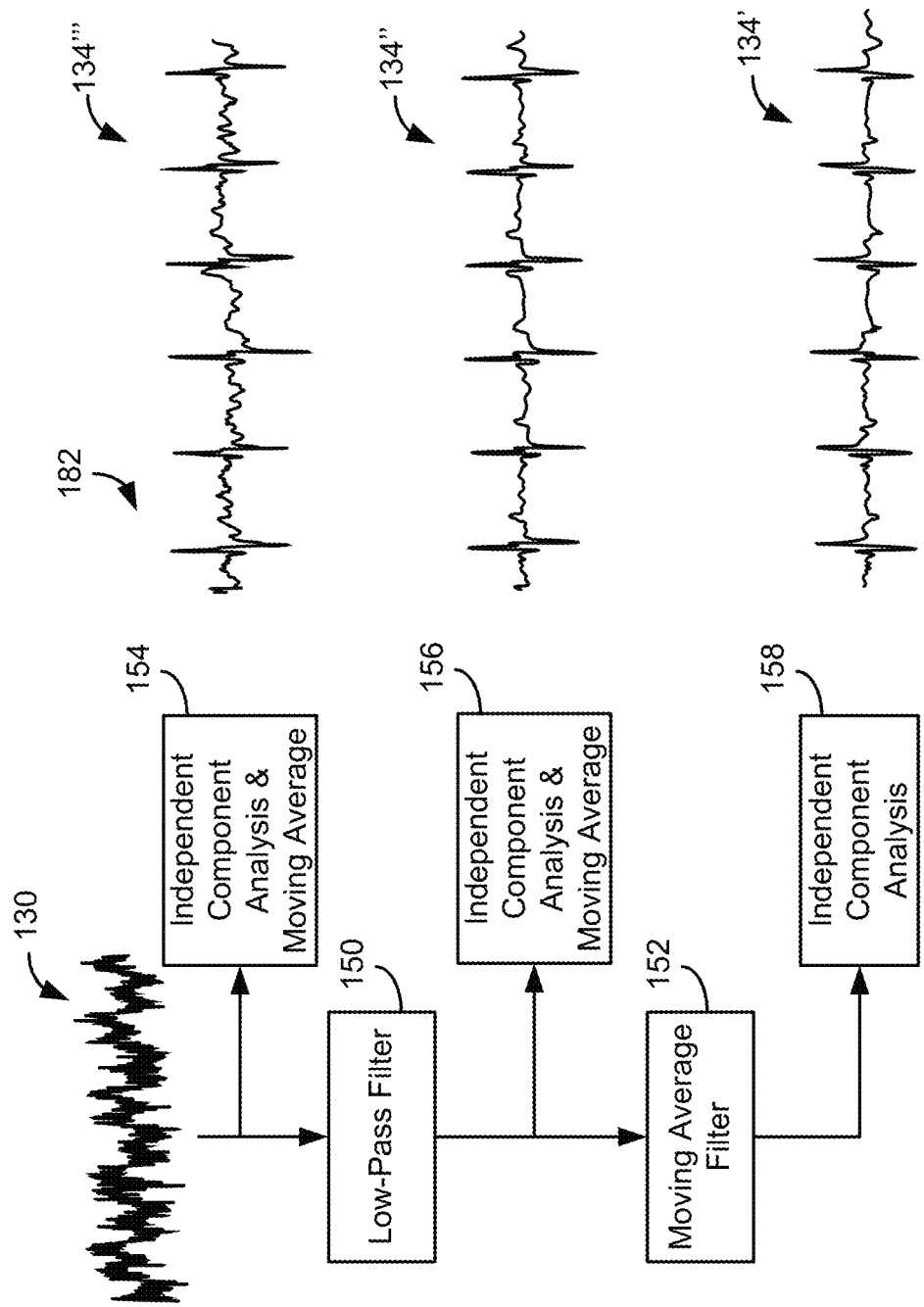
FIG. 9 shows a process for extracting a cardiac signal from a spinal signal that is measured at one or more electrodes that are implanted within a patient's spinal column in accordance with an example of the disclosure.

FIG. 9 shows an alternative process 182, which may form part of the cardiac activity extraction algorithm 132, for extracting a cardiac signal from a spinal signal 130. The process 182 differs from the process 180 in FIG. 8 in that independent component analysis (ICA) is employed on various signals in the process. As is known, independent component analysis is a statistical technique used to extract subcomponents from a multivariate signal. The cardiac signal is a subcomponent of the spinal signal 130 and can be extracted through independent component analysis. In the example shown, independent component analysis is employed on the spinal signal 130 to extract the cardiac subcomponent and a moving average filter is applied (154) to the extracted subcomponent to obtain cardiac signal 134'. Similarly, independent component analysis is employed on the filtered signal 132 to extract the cardiac subcomponent and a moving average filter is applied (156) to the extracted subcomponent to obtain cardiac signal 134". Likewise, independent component analysis is employed (158) on the cardiac signal 134 itself to further isolate the cardiac subcomponent to obtain cardiac signal 134'. As will be understood, the process 182 need not include every independent component analysis step. For example, the process 182 may include one of the paths through one of ICA & moving average filter block 154, ICA & moving average filter block 156, or ICA block 158. As will be understood, the different paths produce different results and require different computational resources, so selecting a desired path involves a balance of these parameters. While independent component analysis is illustrated, it will be understood that principal component analysis (PCA), singular value decomposition (SVD), proper orthogonal decomposition (POD), or other model reduction techniques may also be employed as they are all model reduction schemes that aim to reduce measured data into smaller sets of data key relevant components. In the remainder of this Specification, a cardiac signal or an extracted cardiac signal refers to a cardiac signal extracted from a spinal signal through any of the above-described processes or other signal extraction processes. As illustrated by the processes 180 and 182, the control circuitry 102 of the IPG 100 is configured to process a spinal signal 130 to extract a cardiac signal 134 that comprises one or more features that are representative of the patient's cardiac activity, which features are visible in the cardiac signal 134 without further processing as described below.

The inventors have observed that the cardiac signals 134 that are extracted from monopolar spinal signals 130 for certain lead-based electrodes 16 do not exhibit the same prominent cardiac features that are observed in the cardiac signals 134 that are extracted from monopolar spinal signals 130 for other lead-based electrodes 16. It is believed that these differences in the extracted cardiac signals 134 that are associated with different electrodes 16 occur as a result of the physical positioning of the electrodes relative to the reference as well as common mode noise. Thus, in some instances better results can be obtained through the extraction of cardiac signals 134 from bipolar spinal signals 130 (i.e., voltage differentials between two lead-based electrodes 16), which extraction can be accomplished in the same manners as described above.

A bipolar spinal signal 130 is obtained in a similar manner as a monopolar spinal signal 130 with the exception that the inputs to a sense amplifier 110 are selected (e.g., via the multiplexer 108) to be the two desired lead-based electrodes 16 as opposed to a single lead-based electrode 16 and a reference voltage. The bipolar spinal signal can then be processed in the same manner as described above (e.g., via the processes 180 or 182) to extract a cardiac signal 134. Because spinal signals 130 and their extracted cardiac signal 134 counterparts are vectors having a common direction, and because the location of electrodes 16 are known relative to each other, the electrodes 16 that comprise a bipolar spinal signal 130 can be selected to obtain a cardiac signal 134 having a desired directionality.

Figure 10:
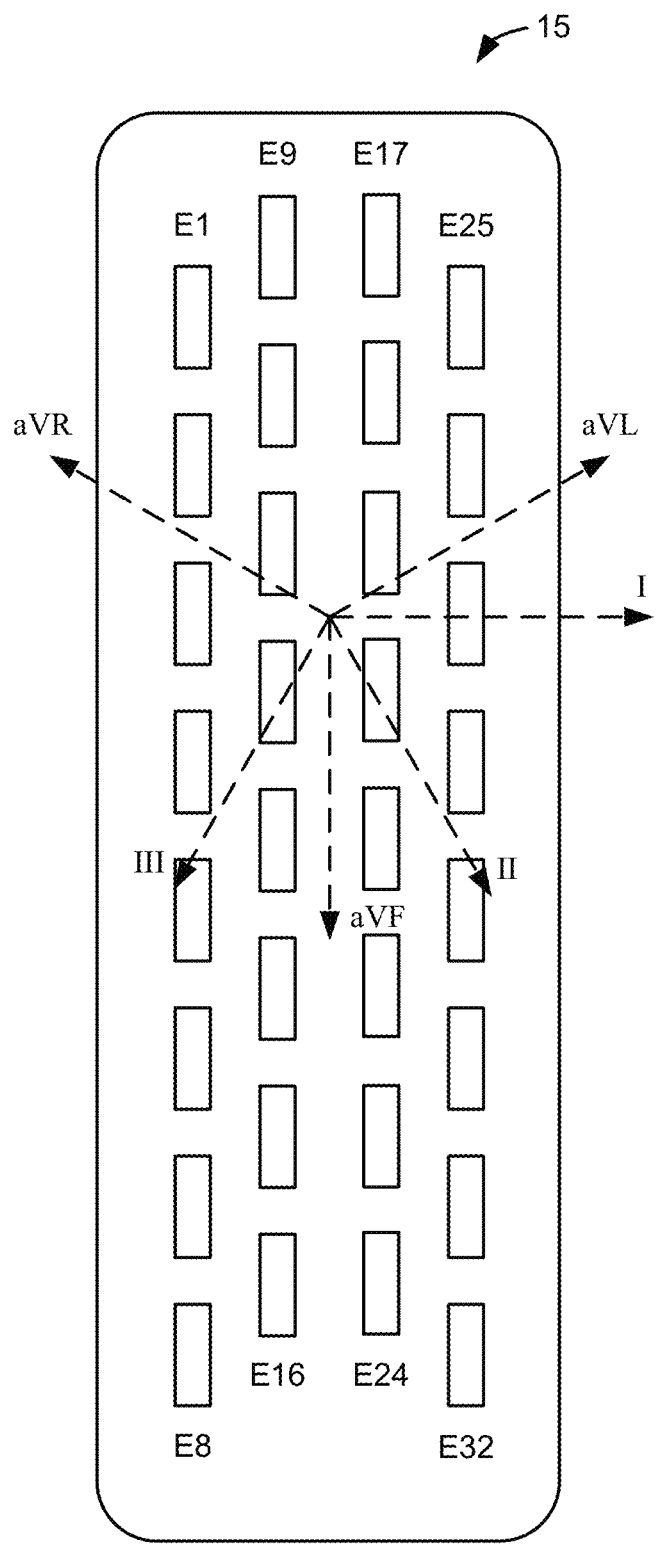
FIG. 10 shows an example paddle lead and the directions of standard electrocardiogram (ECG) limb leads and augmented limb leads in accordance with an example of the disclosure.

FIG. 10 illustrates a paddle lead 15 and the directionality of the limb and augmented limb leads of a standard 12-lead ECG (note that lead direction assumes that the paddle lead 15 is viewed from the posterior to anterior direction). Assuming the paddle lead 15 is aligned with no angular deflection with respect to the patient's anatomical midline, a cardiac signal 134 that is extracted from the bipolar spinal signal 130 that is measured between electrodes E1 and E25 (E25-E1) would match the directionality of the Lead I limb lead of a standard ECG. Note that similar results would be expected for bipolar spinal signals 130 for other pairs of laterally aligned electrodes (e.g., E2 and E26, E3 and E27, etc.). Similarly, a cardiac signal 134 that is extracted from a bipolar spinal signal 130 comprised of vertically-aligned electrodes (e.g., E1 and E8, E9 and E16, etc.) would match the directionality of the augmented vector foot (aVF) limb lead of a standard ECG. The electrodes 16 that comprise bipolar spinal signals 130 can similarly be selected to approximate the directionality of the other illustrated standard limb leads. While a paddle lead 15 is illustrated in FIG. 10, it will be understood that different electrodes can be selected across separate leads (e.g., separate percutaneous leads 14) to obtain bipolar spinal signals 130 having the desired directionality. Moreover, where multiple leads are implanted in different anterior-posterior planes (e.g., as verified via a lateral fluoroscope), electrodes 16 can be selected to obtain bipolar spinal signals 130 (and associated extracted cardiac signals 134) that match the direction of one or more of the standard ECG precordial leads.

Figure 11:
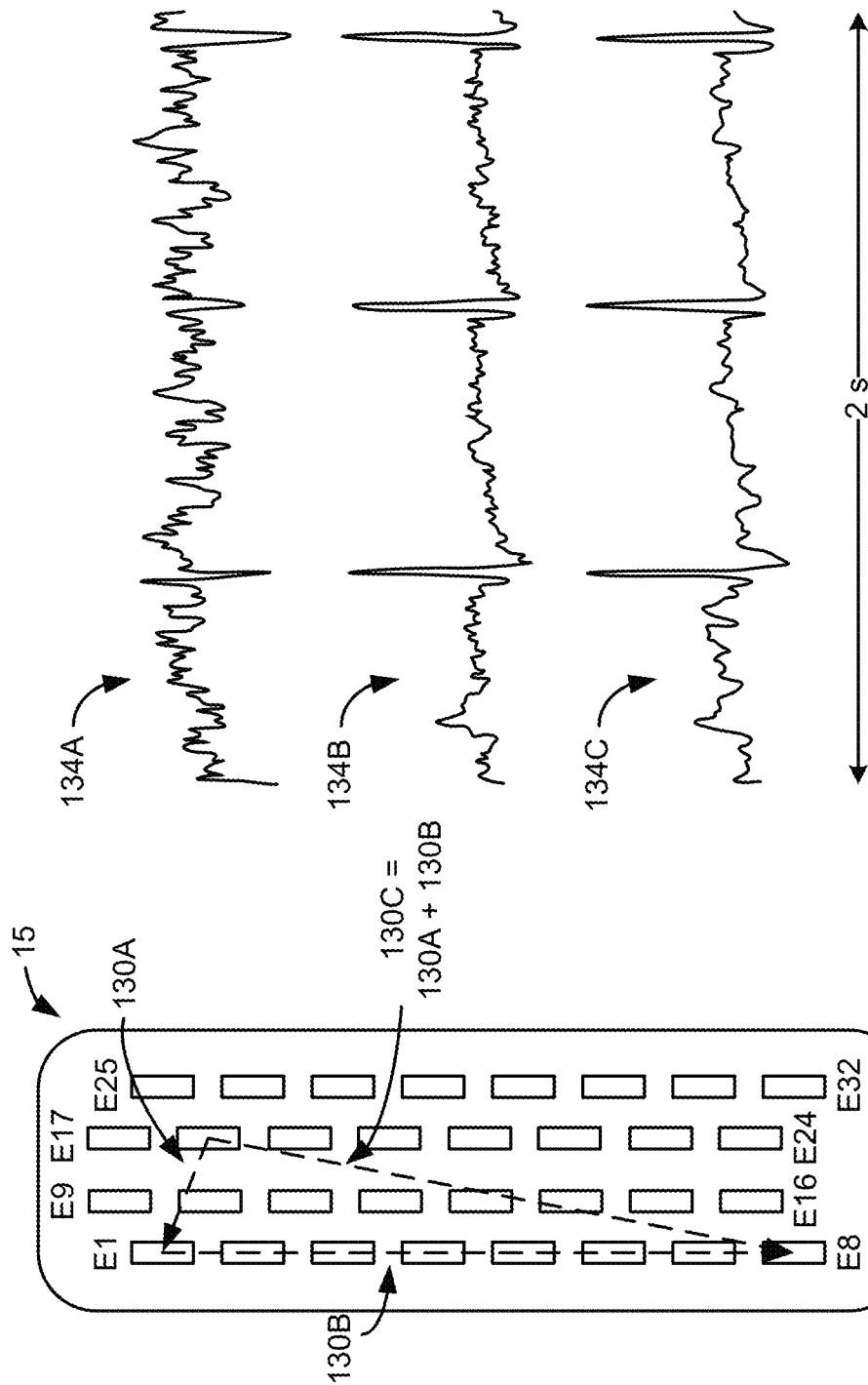
FIG. 11 shows example bipolar spinal vectors, the combination of the bipolar spinal vectors, and the extracted cardiac signals associated with the bipolar spinal vectors and the combination spinal vector in accordance with an example of the disclosure.

Spinal signals 130 can also be arithmetically combined (i.e., added or subtracted) to provide additional benefits in terms of the quality of extracted cardiac signals 134 as well as directional selectivity. FIG. 11 illustrates a cardiac signal 134A that is extracted from a bipolar spinal signal 130A that represents the voltage differential between electrodes E18 and E1 and a cardiac signal 134B that is extracted from a bipolar spinal signal 130B that represents the voltage differential between electrodes E1 and E8. The cardiac features are much less prominent in the cardiac signal 134A than in the cardiac signal 134B due to the proximity of electrodes E1 and E18. When the signals 130A and 130B are added, the resulting combined spinal signal 130C approximates (in magnitude and direction) the voltage differential between electrodes E18 and E8. The cardiac signal 134C that is extracted from the combined spinal signal 130C is perhaps cleaner than either signal 134A or 134B. In fact, combined spinal signals 130 can often be used to extract signals 134 and choose the ones with lesser noise. For example, the spinal signal 134C that is extracted from the combined spinal signal 130C may be less noisy than the cardiac signal 134 that is extracted from the bipolar spinal signal 130 that represents the voltage differential between electrodes E18 and E8.

This technique is especially valuable when a cardiac signal having a desired directionality can only be obtained directly from a bipolar spinal signal 130 between electrodes that are closely positioned. Consider, for example, the extraction of a cardiac signal 134 having a directionality that is aligned with the Lead I limb lead (FIG. 10). As described above, such a cardiac signal 134 can be extracted from a bipolar spinal signal 130 comprised of electrodes that are laterally aligned such as E1 and E25. However, due to the design of the lead 15, any pair of electrodes 16 that are laterally aligned are also positioned relatively close to each other (e.g., E1 and E25, E2 and E26, etc.). As illustrated by the signal 134A in FIG. 11, the cardiac features in a cardiac signal 134 that is extracted from a bipolar spinal signal 130 comprised of electrodes that are in close proximity are less prominent. Thus, as shown in FIG. 12, a more desirable cardiac signal 134 having the same directionality as Lead I might be extracted, for example, from the addition of a first bipolar spinal signal 130D representing the voltage differential between electrodes E1 and E32 and a second bipolar spinal signal 130E representing the voltage differential between electrodes E8 and E25. The resulting combined spinal signal 130F has the desired directionality of Lead I, but it does not suffer from the close proximity of electrodes that would be required to measure a similar spinal signal directly.

Figure 14:
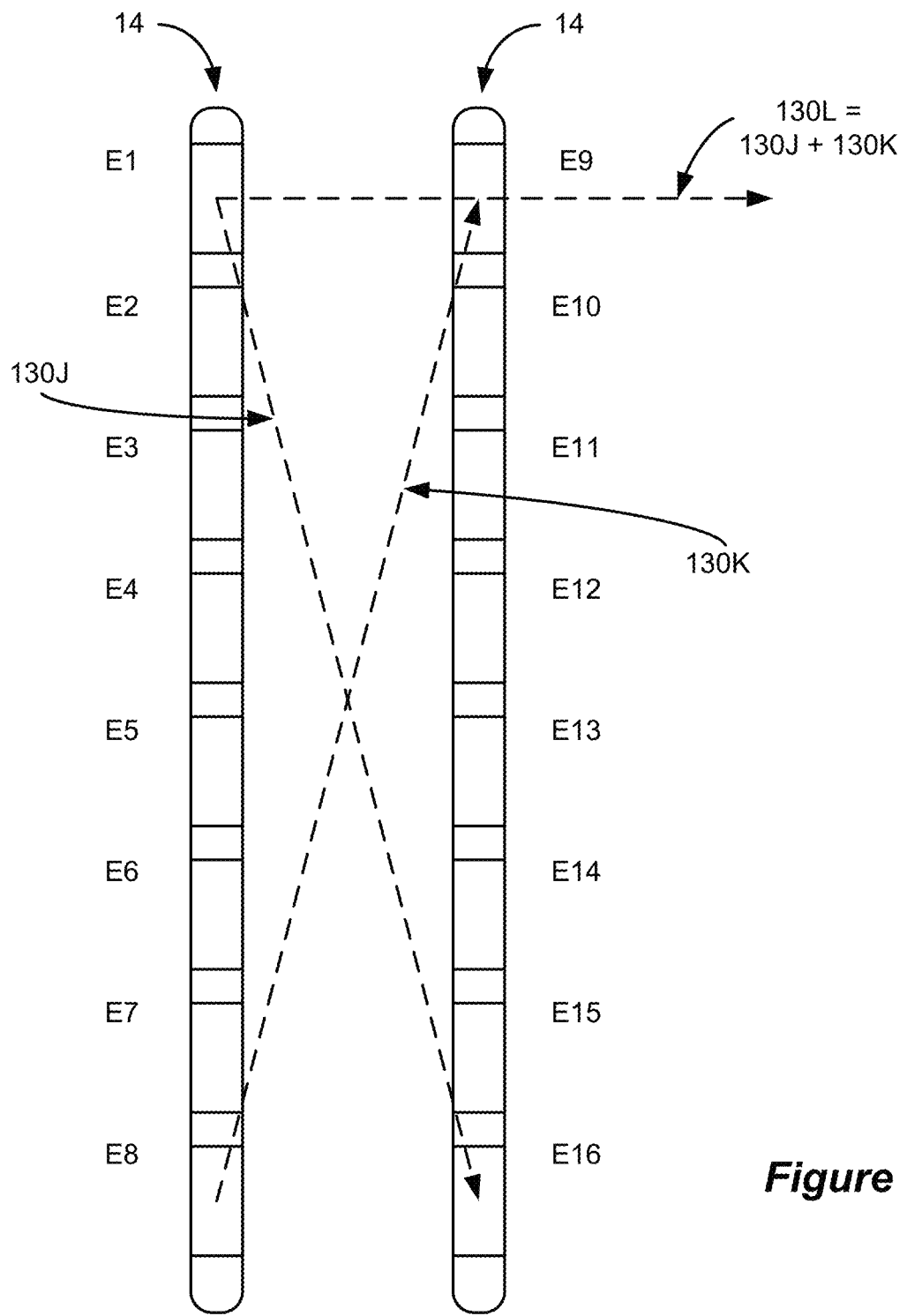

Combined spinal signals 130 can additionally represent a directionality that cannot be obtained through a direct bipolar spinal signal (e.g., where no pair of electrodes is aligned with a desired directionality). As illustrated in FIG. 13, for example, a cardiac signal 134 having a directionality that is aligned with the augmented vector right (aVR) lead can be extracted from a combined spinal signal 130I that is created from the addition of bipolar spinal signal 130G that represents the voltage differential between electrodes E22 and E1 and bipolar spinal signal 130H that represents the voltage differential between electrodes E30 and E8. While combinations of two bipolar spinal signals 130 have been described, it will be understood that combined spinal signals may be created from greater numbers of constituent spinal signals 130. Thus, a cardiac signal 134 having a more precise directionality can be extracted from a combined spinal signal 130 than could be extracted from a bipolar spinal signal 130 comprised of any pair of electrodes. Cardiac signals 134 can be extracted from combined spinal signals 130 in the same manner as described above for monopolar and bipolar spinal signals 130 (e.g., via processes 180 or 182). While spinal signals 130 may be combined prior to cardiac signal extraction, the constituent spinal signals 130 (e.g., the constituent bipolar spinal signal pairs) can be processed to extract cardiac signals 134 and those cardiac signals 134 can be combined to obtain a combined cardiac signal 134, which would have the same directionality as a cardiac signal 134 that is extracted from the combined spinal signal 130 resulting from the combination of the constituent spinal signals 130. While FIGS. 11-13 illustrated and described combined spinal signals in the context of a paddle lead 15, it will be understood that combined spinal signals can be similarly extracted from electrodes that are positioned on different types of leads such as the separate percutaneous leads 14 that are illustrated in FIG. 14.

Figure 15:
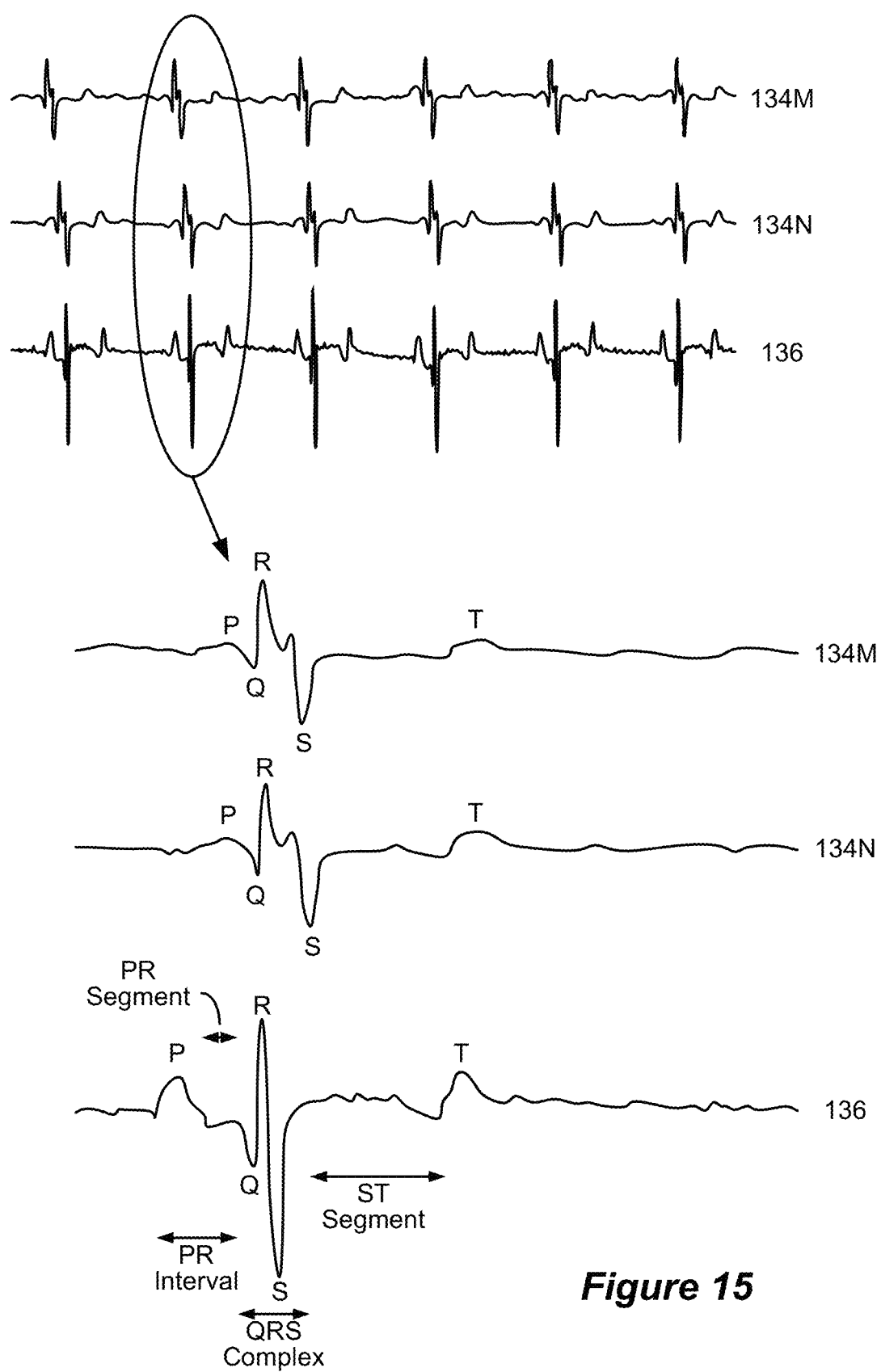
FIG. 15 shows example cardiac signals that were extracted from measured spinal signals and a simultaneously-measured ECG signal in accordance with an example of the disclosure.

Having described the manner in which cardiac signals 134 can be extracted from spinal signals 130 of different types, FIG. 15 illustrates cardiac signals 134M and 134N, which were extracted from two different monopolar spinal signals 130M and 130N, in comparison with a simultaneously-recorded ECG signal 136. As is clearly visible in FIG. 15, each of the signals 134 includes many of the same features as the ECG signal 136. This shows that the extracted cardiac signals 134 carry much of the same information as a traditional ECG. Although the features of the cardiac signals 134 differ slightly from the corresponding features of the ECG signal 136 (e.g., in amplitude, shape, and/or time), in the enlarged portion of FIG. 15 corresponding features between the ECG signal 136 and the cardiac signals 134 are labeled using standard ECG labels. As illustrated, each of the extracted cardiac signals 134 includes portions that mirror the QRS complex in the ECG signal 136. Specifically, the extracted cardiac signals 134 exhibit a decrease, increase, and decrease in amplitude that corresponds to the similar pattern in the Q, R, and S waves in the ECG signal 136. The extracted cardiac signals 134 also exhibit increases in amplitude that correspond to the P and T waves in the ECG signal 136.

As is known, ECG signals such as 136 provide significant information regarding a patient's cardiac activity, and thus the similar patterns in the extracted cardiac signals 134 provide much of the same information. The most elementary information that can be derived from the extracted cardiac signal is the patient's heart rate. The heart rate can be determined based on the time between common features in an extracted cardiac signal 134, which common features represent corresponding cardiac activities for different heartbeats. For example, the heart rate can be identified based on the time between consecutive 'R wave' peaks in a cardiac signal 134 or, stated differently, the number of such peaks in a given time period. Other cardiac parameters such as respiration rate and anomalies such as atrial fibrillation, arrhythmia, ventricular hypertrophy, myocardial infarction, myocardial ischemia, etc. can be detected through more complex analyses of features in the extracted cardiac signal 134 such as QRS amplitude, QRS duration, and ST segment elevation or depression.

These cardiac parameters can be calculated automatically using cardiac analysis algorithms applied to one or more extracted cardiac signals 134, which algorithms may form part of the cardiac activity extraction algorithm 132. The automatically-determined cardiac parameters provide many useful benefits to the patient. A large number of patients that are implanted with spinal cord stimulation devices are in an elevated age bracket in which cardiac monitoring is beneficial. Such patients will greatly benefit from the ability to monitor for cardiac anomalies using the IPG 100 itself. In one embodiment, the IPG 100 may be configured to communicate an indication of a detected cardiac anomaly to an external device such as external controller 50. If the external device is connected to a wide-area network, the indication can be further communicated by the device such as to the patient's physician.

Because the perception of pain affects a patient's cardiac activity, the automatically-detected cardiac parameters such as heart rate and respiration rate provide insight regarding the degree of pain that a patient is experiencing. In one embodiment, the IPG may adjust stimulation parameters based on changes in the detected cardiac parameters. For example, as heart rate and/or respiration rate increase, the IPG 100 may increase stimulation parameters according to a predefined relationship. In an alternate embodiment, the IPG 100 may prompt a patient (e.g., via a communication to an external device such as external controller 50) to adjust stimulation parameters when the detected cardiac parameters increase or decrease by a predetermined amount.

In one embodiment, the IPG 100 may include a motion detector such as an accelerometer or a gyroscope such that the motion of the IPG 100 can be associated with the detected cardiac parameters. Evaluation of the motion sensor enables the IPG 100 to determine whether the patient is engaging in physical activity and to correlate physical activity with the detected cardiac parameters. Based on this established correlation, the IPG 100 can then determine when the cardiac parameters deviate from a normal range for a given level of physical activity such that the stimulation parameters can be automatically adjusted or the patient can be prompted to adjust the stimulation parameters.

Figure 16:
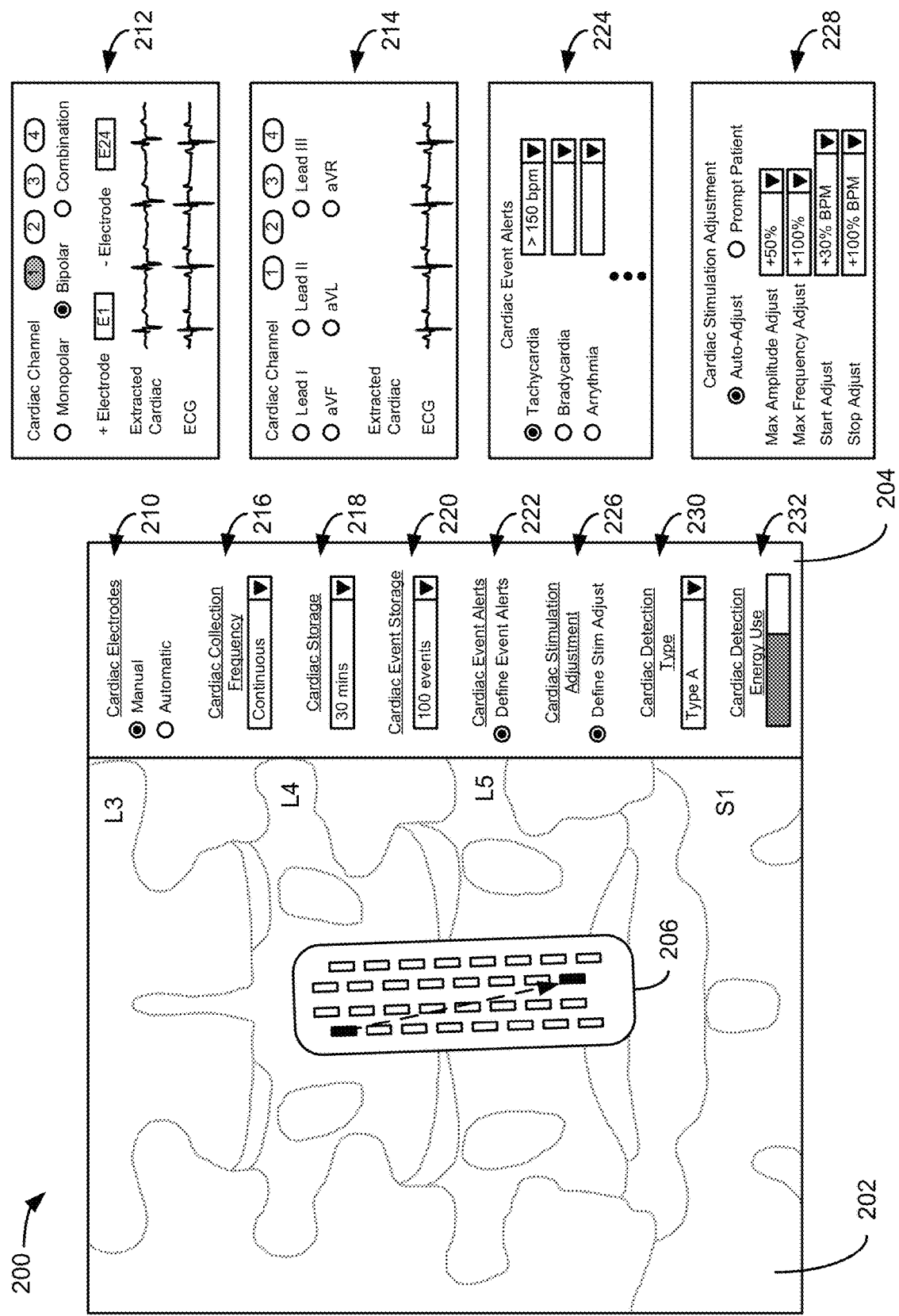
FIG. 16 shows an example graphical user interface that can be used to configure the manner in which an IPG measures spinal signals, extracts cardiac signals from the measured spinal signals, and evaluates the extracted cardiac signals to provide information, alerts, or stimulation adjustments in accordance with an example of the disclosure.

FIG. 16 illustrates a portion of an example graphical user interface 200 that is provided on a clinician programmer 90 to establish cardiac activity detection parameters. The graphical user interface 200 is rendered via the execution of computer program instructions by the clinician programmer computer 96, for example, and the interface 200 is configured to receive one or more user settings for extracting a cardiac signal as described below. The illustrated portion of the GUI 200 includes fluoroscopic image 202, which shows the one or more implanted leads relative to anatomical structures, such as vertebrae. Using the illustrated interface, a user can select a representation of the implanted electrode lead from an electrode lead portion of the interface 200 (not shown), which includes representations of various types of lead products such as a 1×8 percutaneous lead, a 1×16 percutaneous lead, and a 4×8 paddle lead. The user can then drag the lead representation 206 for the one or more implanted leads onto the fluoroscopic image 202 and manipulate its size and orientation until it aligns with the implanted electrode lead in the image 202. Because the representations 206 are programmed with properties of the lead such as electrode size, shape, and spacing, the positioning of a lead representation 206 on the fluoroscopic image 202 relates the locations of the electrodes 16 to the image 202. This enables the software operating on the clinician programmer 90 to understand the location of the electrodes 16 with respect to anatomical features such as the anatomical midline. This is particularly useful for visualizing the anatomical location of stimulation for a given set of stimulation parameters, but the electrodes' anatomical locations can also be used in configuring cardiac activity detection parameters.

The cardiac activity detection interface 204 includes multiple interfaces for configuring cardiac activity detection parameters. The cardiac electrode selector 210 enables the user to select either manual electrode configuration or automatic electrode configuration to specify the electrode settings that will be communicated to the IPG 10 to measure a spinal signal. When manual electrode configuration is selected, the user can access a manual electrode configuration interface 212 that enables the user to manually select the electrodes 16 that are used to measure spinal signals 130 from which cardiac signals 134 are extracted. In the illustrated embodiment, the user can manually configure up to four different cardiac channels (i.e., up to four different electrode configurations to produce different cardiac signals 134), but it will be understood that the graphical user interface 200 and the IPG 100 may be configured to accommodate more or fewer cardiac channels. For each cardiac channel, the user is provided with an option to select a monopolar, bipolar, or combination electrode arrangement. Based on the selected type of electrode arrangement, the manual electrode configuration interface 212 enables the user to select desired electrodes. For example, in the illustrated embodiment, the user has selected a bipolar electrode arrangement for cardiac channel 1. Based on this selection, the manual electrode configuration interface 212 enables the user to select the positive and negative electrodes that will comprise the bipolar spinal signal 130 from which the cardiac signal 134 for cardiac channel 1 will be extracted. The user may make these selections by entering (e.g., typing an electrode identifier) the desired electrodes in the appropriate fields in the interface 212 or by selecting the desired electrodes on the lead representation 206 that overlays the fluoroscopic image 202. In the illustrated embodiment, the selected electrodes are highlighted and the directionality of the spinal signal 130 is illustrated on the lead representation 206. When the electrode parameters to be used for cardiac activity detection have been communicated to the IPG 100 and the IPG 100 is implementing the parameters, the extracted cardiac signal 134 for the selected channel is communicated to the CP programmer and is displayed in the interface 212. This enables the user to evaluate the quality of the cardiac signal 134 that is obtainable for the current selections in near real time. In the illustrated embodiment, a simultaneously-recorded ECG is also illustrated in the interface 212 to enable a comparison of the extracted signal.

When automatic electrode configuration is selected, the user can access an automatic electrode configuration interface 214 that is substantially similar to the manual electrode configuration interface 212. The automatic electrode configuration interface 214, however, enables the user to select from one of several predefined cardiac leads. In the illustrated embodiment, the interface 214 enables selection of one of the six standard limb and augmented limb leads for each of the four cardiac channels, but it will be understood that other predefined cardiac signal types could be made available for selection. When the user selects an automatic configuration, the software executing on the clinician programmer ("CP") 90 uses the known anatomical location of the electrodes to determine the particular electrode arrangement (e.g., monopolar, bipolar, or combination) that most closely matches the directionality of the selected configuration. For example, the CP software accounts for any angular offset of the one or more implanted leads (based on the lead representations 206) to identify an electrode arrangement that is most closely aligned with the directionality of the selected configuration. When multiple different electrode arrangements have directionalities that are the same or similar to the selected configuration, the CP software determines the most appropriate electrode arrangement from this group. In one embodiment, the CP software may be configured to select the most appropriate electrode arrangement according to a set of rules that are based on assumptions and preferences (e.g., preference given to electrodes that are spaced further apart, etc.). In another embodiment, the CP software may be configured to select the most appropriate electrode arrangement by requesting extracted cardiac signals 134 for the different electrode arrangements from the IPG 100 and evaluating the received signals to determine the most appropriate electrode arrangement (e.g., determining which electrode arrangement results in the highest quality extracted cardiac signal 134). After the appropriate electrode arrangement is determined, the electrode parameters may be transmitted to the IPG 100 and the extracted cardiac signal 134 that is associated with the determined parameters may be displayed in the interface 214 for comparison with a simultaneously-recorded ECG in the same manner as in the interface 212 (note that no extracted cardiac signal is shown in the interface 214 in the illustrated embodiment because cardiac channel 1 is shown as being selected to manual configuration). While the illustrated interface 204 indicates that either manual or automatic electrode configuration can be selected, in one embodiment, the two different electrode configuration types can be mixed on a cardiac channel basis (e.g., cardiac channel 1 may include a manual configuration while cardiac channel 2 includes an automatic configuration, etc.). The configured cardiac channels can be used in combination to determine the cardiac parameters (e.g., heart rate, heart rate variability, ST segment elevation, respiration rate, etc.) and to detect cardiac events.

The cardiac extraction interface 204 additionally includes a cardiac collection frequency selector 216 and a cardiac storage trigger (event detection trigger, schedule time of the day, patient trigger, or other). The selector 216 enables the user to determine how frequently cardiac signals 134 are extracted from measured spinal signals 130. For example, cardiac signals 134 may be extracted and evaluated continuously, for a 15 second period every minute, for a 15 second period every 5 minutes, for a 15 second period every 15 minutes, etc. As will be understood, because cardiac signal extraction requires significant processing, increased frequency results in increased energy use and thus shorter battery life in the IPG 100.

The extracted cardiac signals 134 and associated detected cardiac events can be stored in a memory within the IPG 100 for later retrieval by an external device such as external controller 50 or clinician programmer 90. The cardiac storage frequency selector 218 enables the user to determine the duration of cardiac signals that should be maintained in the IPG 100's memory. For example, the user may select to store the most recent 10 minutes, the most recent 30 minutes, the most recent one hour, etc. of each of the extracted cardiac signals (i.e., the cardiac signal associated with each cardiac channel). The cardiac signals may be downsampled before being stored to save memory, and, in one embodiment, downsampling settings may also be customizable via settings in the cardiac activity detection interface 204. When the selected cardiac storage limit is reached, older portions of recorded cardiac signals 134 may be deleted from the IPG 100's memory as more recent portions are stored.

The cardiac event storage selector 220 enables the user to select the number of cardiac events that are stored in the IPG 100's memory (e.g., the 20 most recent events, the 50 most recent events, the 100 most recent events, etc.). The data associated with cardiac events may include a text identification (e.g., tachycardia, bradycardia, etc.) and the date, time, and related value (e.g., 147 beats per minute) of the detected event. In one embodiment, the cardiac event may also include a short segment (e.g., 15 seconds) of the one or more cardiac signals 134 that led to the detection regardless of whether the one or more signals are additionally stored as part of the cardiac signal storage. Just as with the cardiac signal storage, when the number of events in the IPG 100's memory reaches the selected value, the data associated with older events may be deleted from the IPG 100's memory as more recent events are stored.

The cardiac event alerts selector 222 enables the user to define which events result in alerts being communicated to an external device such as external controller 50. When the user selects to define event alerts using the selector 222, an event alert definition interface 224 is displayed. The event alert definition interface 224 enables the user to select the types of events (e.g., tachycardia) for which an alert should be communicated to an external device and, for the selected types of events, to select a parameter limit (e.g., >150 beats per minute) at which the event alert should be communicated. In one embodiment, the types of events and associated limits that are selected via the event alert definition interface 224 define the events and associated limits that result in events being stored in the IPG 100's memory. In another embodiment, the events that are stored in memory are set by default and the event alerts and associated limits are treated separately as defined in the event alert definition interface 224.

The cardiac stimulation adjustment selector 226 enables the user to specify whether and how stimulation parameters are to be adjusted based on extracted cardiac signals. When the user selects to enable stimulation adjustment using the selector 226, a stimulation adjustment definition interface 228 is displayed. The stimulation adjustment definition interface 228 enables the user to select whether stimulation adjustments should be made automatically or whether the user should be prompted to approve stimulation adjustments based on detected cardiac parameters. The interface 228 additionally enables the user to select the maximum amount by which stimulation parameters can be adjusted based on detected cardiac parameters. For example, in the illustrated embodiment, the user has selected a maximum stimulation amplitude adjustment of 50% of the baseline stimulation amplitude and a maximum stimulation frequency adjustment of 100%. The interface 228 additionally enables the user to select the cardiac parameter range over which the stimulation adjustments are implemented. In the illustrated embodiment, the stimulation adjustments are to be initiated when the detected heart rate is 30% above the average heart rate and at the maximum values when the detected heart rate is 100% above the average hear rate where the average heart rate may be programmable or extracted over a predefined or programmable time window. Based on the examples in the illustrated embodiment, assuming a baseline stimulation amplitude of 4.0 mA and an average heart rate of 80 beats per minute, the stimulation amplitude would increase according to a programmable function (e.g., linear, exponential, piecewise function or other) from 4.0 mA to 6.0 mA as the detected heart rate increased from 104 to 160 beats per minute. Similarly, assuming a baseline stimulation frequency of 400 Hz, the stimulation frequency would increase according to a programmable function from 400 Hz to 800 Hz as the detected heart rate increased from 104 to 160 beats per minute. As will be understood, the stimulation parameter adjustments could also be defined in different ways and the relationship between the detected cardiac parameter and the stimulation adjustment parameter could be an inverse relationship as opposed to the direct relationship examples given. If the user selects the patient prompt selector in the interface 228, the patient would be prompted (e.g., via a communication to the external controller 50) to accept a stimulation adjustment based on detected cardiac parameters. As noted above, stimulation adjustment may also incorporate input from a motion sensor such as an accelerometer, and, in such an embodiment, settings that specify the manner in which the motion sensor is utilized in stimulation adjustments based on detected cardiac parameters may be specified within the interface 228.

The cardiac detection type selector 230 enables the user to specify the manner in which cardiac signals 134 are to be extracted from measured spinal signals 130. For example, the selector 230 may list a number of extraction techniques such as portions of the processes 180 and 182 and various settings of the different processing blocks in those processes to enable the user to select and customize an extraction technique. Using the cardiac detection type selector 230 in conjunction with the electrode selector 210 and electrode configuration interfaces 212 and 214 enables the user to determine the particular settings that produce the highest quality extracted cardiac signals 134, which settings will differ from patient to patient.

The cardiac detection energy use indicator 232 provides a representation of the relative energy use associated with the selected cardiac detection settings. As will be understood, the various selected cardiac detection settings (e.g., cardiac detection type, quantity and configuration of the cardiac channels, cardiac collection frequency, etc.) influence the processing requirements for carrying out the desired cardiac detection, which, in turn, influences the amount of energy that will be utilized by the IPG 100 to implement the settings. The cardiac detection energy use indicator 232 enables the user to balance the quality of the extracted cardiac signals 134 (e.g., as visualized through the electrode configuration interfaces 212 or 214) with the amount of energy required to obtain the desired cardiac signals 134. In the illustrated embodiment, the cardiac detection energy use indicator 232 is presented as a bar that represents the relative amount of energy use for cardiac activity detection from a minimum value to a maximum value. It will be understood that energy use can be depicted in different ways as well. The CP software is configured to communicate the settings that are configured via the cardiac activity detection interface 204 to the IPG 100 via a communication link between the clinician programmer 90 and the IPG 100. Upon receiving the user settings, the IPG measures one or more spinal signals 130 and extracts one or more cardiac signals 134 based upon the received settings.

Figure 17:
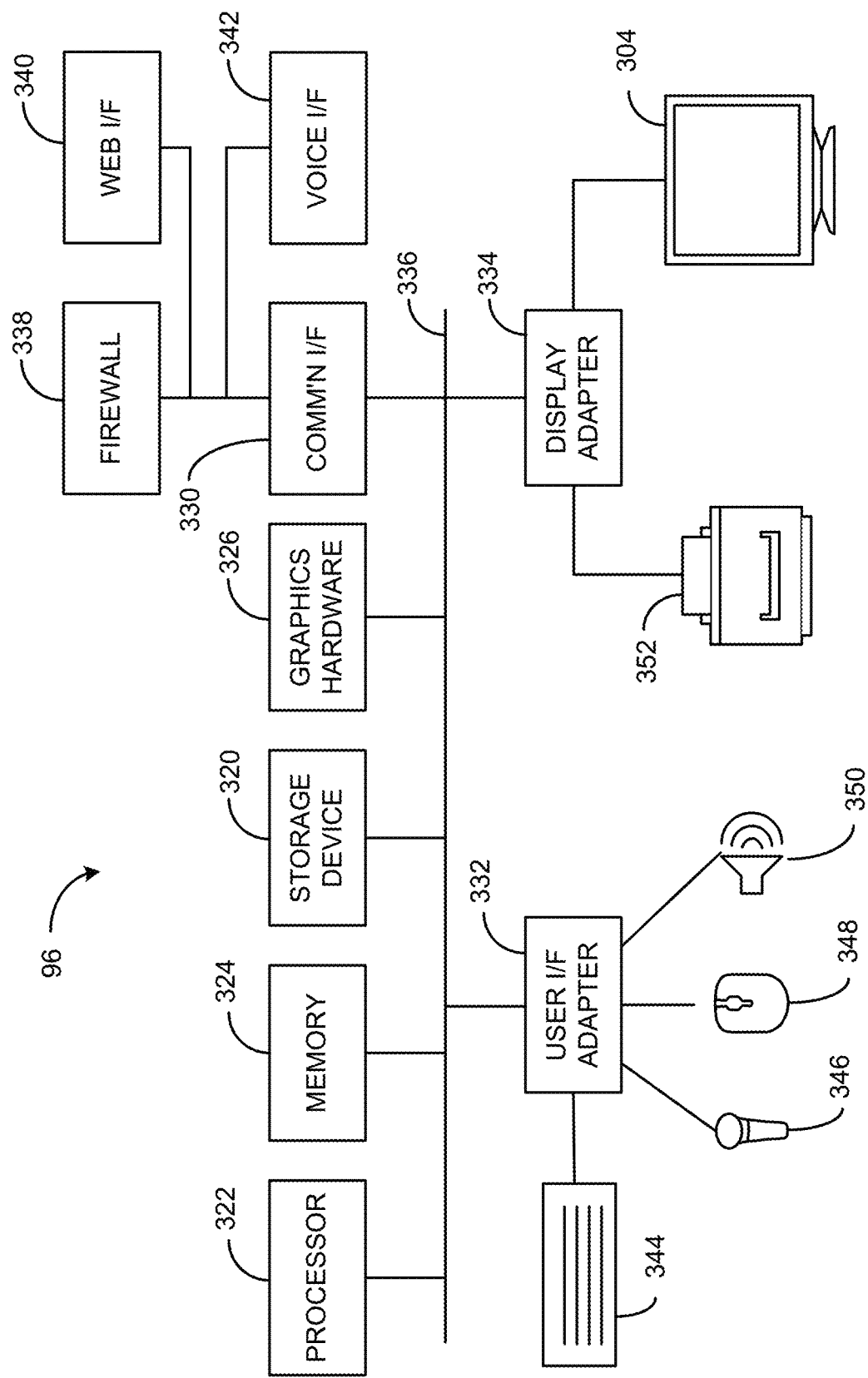
FIG. 17 illustrates a representative computing environment on which software that provides an interface for configuring the manner in which cardiac signals are extracted from measured spinal signals may be executed in accordance with an aspect of the disclosure.

FIG. 17 illustrates the various components of an example CP computer 96 that may be configured to execute CP software for providing, for example, the graphical user interface 200. The CP computer 96 can include a processor 322, memory 324, storage 320, graphics hardware 326, communication interface 330, user interface adapter 332 and display adapter 334—all of which may be coupled via system bus or backplane 336. Memory 324 may include one or more different types of media (typically solid-state) used by the processor 322 and graphics hardware 326. For example, memory 324 may include memory cache, read-only memory (ROM), and/or random access memory (RAM). Storage 320 may store media, computer program instructions or software (e.g., CP software), preference information, device profile information, and any other suitable data. Storage 320 may include one or more non-transitory computer-readable storage mediums including, for example, magnetic disks (fixed, floppy, and removable) and tape, optical media such as CD-ROMs and digital video disks (DVDs), and semiconductor memory devices such as Electrically Programmable Read-Only Memory (EPROM), Electrically Erasable Programmable Read-Only Memory (EEPROM), and USB or thumb drive. Memory 324 and storage 320 may be used to tangibly retain computer program instructions or code organized into one or more modules and written in any desired computer programming language. As will be understood, the CP software (i.e., the CP software that is executable to present the GUI 200 and to communicate the received user settings to the IPG 100) may be stored on a medium such as a CD or a USB drive, pre-loaded on a computing device such as the CP computer 96, or made available for download from a program repository via a network connection. Communication interface 330 may be used to connect the CP computer 96 to a network. Communications directed to the CP computer 96 may be passed through a protective firewall 338. Such communications may be interpreted via web interface 340 or voice communications interface 342. Illustrative networks include, but are not limited to: a local network such as a USB network; a business' local area network; or a wide area network such as the Internet. User interface adapter 332 may be used to connect a keyboard 344, microphone 346, pointer device 348, speaker 350 and other user interface devices such as a touch-pad and/or a touch screen (not shown). Display adapter 334 may be used to connect display 304 and printer 352. Processor 322 may include any programmable control device. Processor 322 may also be implemented as a custom designed circuit that may be embodied in hardware devices such as application specific integrated circuits (ASICs) and field programmable gate arrays (FPGAs). The CP computer 96 may have resident thereon any desired operating system.

While the GUI 200 has been described in terms of its presentation on a clinician programmer 90, it will be understood that a similar interface that enables similar parameter selections may be provided via execution of software on a different type of external device, which device can take the form of a dedicated device (e.g., external controller 50) or an application residing on a smart phone or other personal device that may include various ones of the components described with respect to FIG. 17. Likewise, although spinal signal measurement and processing to extract cardiac signals has been described as being performed on the neurostimulator (e.g., the IPG 100 or ETS 170), it may alternatively be executed on an external device such as the CP computer 96 (e.g., as part of computer program instructions that are executed by the CP computer), external controller 50, or another personal device that includes an application for performing the described processes. In such an embodiment, the external device may include measurement circuitry to measure spinal signals (e.g., instruct the IPG 100 or ETS 170 to measure spinal signals and communicate the digitized spinal signals 130 to the external device) and processing circuitry to process the spinal signals 130 that are received from the neurostimulator to extract cardiac signals 134. Such measurement and processing circuitry may also be referred to as control circuitry.

While various specific embodiments and applications have been described for purposes of illustration, numerous modifications and variations could be made by those skilled in the art without departing from the scope of the invention set forth in the claims.

What is claimed is:

1. A system comprising:
   control circuitry configured to control stimulation circuitry to provide electrical stimulation to one or more electrodes that are connectable to a neurostimulator and implantable within a patient's spinal canal;
   measurement circuitry configured to measure a spinal signal at one or more of the electrodes, wherein the spinal signal comprises a neural response to the electrical stimulation; and
   processing circuitry configured to process the spinal signal to extract a cardiac signal that comprises one or more features that are representative of the patient's cardiac activity.

2. The system of claim 1, wherein the processing circuitry is configured to process the spinal signal using one or more of a low-pass filter, a moving average filter, or a model reduction scheme to extract a cardiac signal.

3. The system of claim 1, wherein the measurement circuitry is within the neurostimulator.

4. The system of claim 3, wherein the processing circuitry is within the neurostimulator.

5. The system of claim 3, wherein the control circuitry is within the neurostimulator.

6. The system of claim 1, wherein the control circuitry is further configured to adjust parameters of the electrical stimulation based on one or more properties of the cardiac signal.

7. The system of claim 1, wherein the processing circuitry is further configured to process the spinal signal by:
   performing a first filtering operation using a low-pass filter; and
   performing a second filtering operation using a moving average filter.

8. The system of claim 1, wherein the processing circuitry is further configured to process the spinal signal by extracting a subcomponent of the spinal signal using a model reduction scheme.

9. The system of claim 8, wherein the model reduction scheme comprises independent component analysis.

10. The system of claim 1, wherein the spinal signal comprises a monopolar spinal signal that is measured as a differential voltage between one of the electrodes and a reference voltage.

11. The system of claim 1, wherein the spinal signal comprises a bipolar spinal signal that is measured as a differential voltage between two of the electrodes.

12. The system of claim 1, wherein the spinal signal comprises an arithmetic combination of two or more bipolar spinal signals that are each measured as a differential voltage between two of the electrodes.

13. The system of claim 12, wherein the two or more bipolar spinal signals are selected to obtain a desired directionality of the spinal signal.

14. The system of claim 1, wherein the processing circuitry is further configured to determine the patient's heart rate based on the cardiac signal.

15. The system of claim 1, wherein the processing circuitry is further configured to detect a cardiac anomaly based on the cardiac signal.

16. The system of claim 15, wherein the system further comprises control circuitry configured to communicate an indication of the cardiac anomaly to the patient.

17. A method comprising:
   providing electrical stimulation to one or more electrodes that are connectable to a neurostimulator and implantable within a patient's spinal canal;
   measuring a spinal signal at one or more of the electrodes, wherein the spinal signal comprises a neural response to the electrical stimulation; and
   processing the spinal signal to extract a cardiac signal that comprises one or more features that are representative of the patient's cardiac activity.

18. The method of claim 17, wherein processing the spinal signal comprises using one or more of a low-pass filter, a moving average filter, or a model reduction scheme to extract the cardiac signal.

* * * * *